United States Patent
Kim et al.

(10) Patent No.: US 9,512,488 B2
(45) Date of Patent: Dec. 6, 2016

(54) METHOD FOR MULTIPLEX-DETECTING CHRONIC MYELOGENOUS LEUKEMIA GENE USING CLEAVABLE PROBE

(71) Applicant: Samsung Life Public Welfare Foundation, Seoul (KR)

(72) Inventors: Kwang Woo Kim, Gyeongsangnam-do (KR); Jong Won Kim, Seoul (KR); Do Hyun Nam, Seoul (KR); Chang-Seok Ki, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 85 days.

(21) Appl. No.: 14/371,255

(22) PCT Filed: Jan. 9, 2013

(86) PCT No.: PCT/KR2013/000140
§ 371 (c)(1),
(2) Date: Jul. 9, 2014

(87) PCT Pub. No.: WO2013/105775
PCT Pub. Date: Jul. 18, 2013

(65) Prior Publication Data
US 2015/0038360 A1    Feb. 5, 2015

(30) Foreign Application Priority Data
Jan. 9, 2012 (KR) .................. 10-2012-0002466

(51) Int. Cl.
*C12P 19/34* (2006.01)
*C12Q 1/68* (2006.01)

(52) U.S. Cl.
CPC .......... *C12Q 1/6886* (2013.01); *C12Q 1/6851* (2013.01); *C12Q 2600/158* (2013.01); *C12Q 2600/16* (2013.01)

(58) Field of Classification Search
USPC ............................ 435/6.12, 91.2; 536/24.33
See application file for complete search history.

(56) References Cited

U.S. PATENT DOCUMENTS 7,700,279 B2    4/2010    Tseng et al.

FOREIGN PATENT DOCUMENTS

KR    10-2008-0004514 A    1/2008

OTHER PUBLICATIONS

Lowe et al. (Nucleic acid research, 1990, vol. 18(7), p. 1757-1761).*
Nucleic acid research reports reports (AC AM491359& AC AM491361), 2015.*
Wikipedia ( Taq polymerase), 2015.*
Nuleic acid sequence search reports (AC: AM491359, AM491361, AM491360, AM491363).*
Harvey, John J. et al.: "Characterization and applications of CataCleave probe in real-time detection assays", *Analytical Biochemistry*, 333 (2004), pp. 246-255.
Burmeister, Thomas et al.: "A multiplex PCR for improved detection of typical and atypical BCR-ABL fusion transcripts", *Leukemia Research*, 32 (2008), pp. 579-585.
Renault, Ilana Zalchberg et al.: "The significance of major and stable molecular responses in chronic myeloid leukemia in the tyrosine kinase inhibitorera", *Rev Bras Hematol Hemoter*, 2011;33(6), pp. 455-460.
Tkachuk, D.C. et al.: "Detection of *bcr-abl* Fusion in Chronic Myelogeneous Leukemia by in Situ Hybridization", *Science*, vol. 250(4980), Oct. 26, 1990, pp. 559-562.
Dobrovic, A. et al.: "Detection of the molecular abnormality in chronic myeloid leukemia by use of the polymerase chain reaction", *Blood*, 1988, 72, pp. 2063-2065.
Lee, MS. et al.: "Detection of two alternative bcr/abl mRNA junctions and minimal residual disease in Philadelphia chromosome positive chronic myelogenous leukemia of polymerase chain reaction", *Blood*, 1989, 73, pp. 2165-2170.
Genbank Accession No. NM_021574.2, "*Homo sapiens* breakpoint cluster region (BCR), transcript variant 2, mRNA", Dec. 18, 2011.
Genbank Accession No. NM_005157.4, "*Homo sapiens* c-abl oncogene 1, non-receptor tyrosine kinase (ABL1), transcript variant a, mRNA", Dec. 24, 2011.
Hessner, Martin J. et al.: "Development of a Sensitive, Highly Controlled Assay for MolecularDetection of the Philadelphia Chromosome in Patients with Chronic Myelogenous Leukemia", *GATA*, 11(4), 1994, pp. 90-94.

* cited by examiner

*Primary Examiner* — Kenneth Horlick
(74) *Attorney, Agent, or Firm* — McCarter & English, LLP

(57) ABSTRACT

One embodiment of the present invention provides a detection kit for detecting a chronic myelogenous leukemia (CML) gene expression, wherein the detection kit includes a primer set which is specifically bound to the CML gene; and a cleavable probe which is specifically bound to the inside of a CML gene amplification product which is amplified by the primer set. Another embodiment of the present invention provides a method of measuring the CML gene expression by using the detection kit according to one embodiment of the present invention. The method according to one embodiment of the present invention is used to efficiently detect a low CML gene expression for CML diagnosis and prognosis diagnosis.

12 Claims, 17 Drawing Sheets

METHOD FOR MULTIPLEX-DETECTING CHRONIC MYELOGENOUS LEUKEMIA GENE USING CLEAVABLE PROBE

This application is a 371 of PCT/KR2013/000140 filed on Jan. 9, 2013, published on Jul. 18, 2013 under publication number WO 2013/105775, which claims priority benefits from Korean Patent Application Number 10-2012-0002466 filed Jan. 9, 2012, the disclosure of which is incorporated herein by reference.

TECHNICAL FIELD

The present invention relates to a chronic myelogenous leukemia gene diagnosis kit and a diagnosis method using the same. More specifically, the present invention relates to a kit enabling to detect a gene in real-time by using a primer set and a cleavable probe, and a diagnosis method using the same.

DESCRIPTION OF THE RELATED ART

Leukemia refers to all diseases in which leukocytes proliferate neoplastically. Leukemia is divided into 'myelogenous leukemia' and 'lymphatic leukemia' with reference to the leukocytes from which leukemia is originated, or into acute leukemia and chronic leukemia with reference to the rate of progress. The clinical patterns of leukemia are various according to the types of the disease and the characteristics of the invaded cells. Lymphatic leukemia is caused by the mutation of lymphatic blood cell, myelogenous leukemia is caused by the mutation of myelogenous blood cells, and chronic myelogenous leukemia (CML) is caused by the mutation of mature cells, in other words, by malignant clones of a pluripotent hematopoietic stem cell. Acute myelogenous leukemia is caused by the defect of a myeloblastic stem cell which begins to differentiate from an earlier stage of hematopoiesis.

Among these different types of leukemia, CML is a malignant hematodyscrasia in which myeloblast cells proliferate in bone marrow and invade peripheral blood or other organs, and the incidence of CML is high in adults. The most important thing to diagnose CML is to detect the Philadelphia chromosome by performing a chromosome test which results in a positive finding in 95% or higher of the patients.

Various causes of CML have been identified, but the most general cause of CML is known to a translocation of a chromosome. In particular, translocation of chromosome 9 and chromosome 22 has been known as the principal cause of CML. In practice, a reciprocal translocation of chromosome 9 and chromosome 22 is found in about 95% of the CML patients. The reciprocal translocation is formed by transfer of a part of the abl (abelson oncogene) gene located at the q34 region of chromosome 9 to the bcr (breakpoint cluster region) gene located at the q11.2 region of chromosome 22. This rearrangement is called BCR-ABL rearrangement. For CML caused by the BCR-ABL rearrangement, imatinibmesylate, which is commercially available in the brand name of Glivec™, is a special efficient medicine having an excellent therapeutic effect. Therefore, early diagnosis of the BCR-ABL rearrangement is very important in deciding the direction of patient treatment and prognosis.

To detect the BCR-ABL rearrangement, a method of quantifying the degree of recombination of the BCR-ABL fusion gene is usually used. Various studies are conducted to develop a method of quantifying the degree of recombination of the BCR-ABL fusion gene in a more convenient way. For example, a diagnosis method using FISH (fluorescent in situ hybridization) (Tkachuk et al., Science, 250(4980): 559-562, 1990), a method using PCR of somatic cell DNA (Dobrovic et al., Blood, 72(6): 2063-2065, 1998), a method using RT-PRC (Lee et al., Blood, 73(8): 2165-2170, 1989), and a method using nested PCR (Hessner et al., Genet. Anal. Tech. Appl., 11(4): 90-94, 1994) have been developed.

However, among the methods listed above, the FISH-based method is for directly detecting individual cells where the BCR-ABL rearrangement has already taken place, and thus the FISH-based method does not allow an early detection of CML. The RT-PCR method has high sensitivity but requires a cytogenetic method, since it is generally difficult to design a primer set which allows for diagnosing a patient having a very rare CML. For this reason, in cases of a patient who is suspected to have CML, various cytogenetic methods are performed from an early stage of diagnosis. However, a cytogenetic method includes many constraints: a cytogenetic method may be performed only after cell cycle of the myeloplast reaches the 'metaphase,' various conditions such as extraction and culture of proliferated cells should be met, and the quantity of the proliferated cells should be sufficient. In addition, a conventional RT-PCR method is complicated, since independent reactions should be performed according to the types of the BCR-ABL gene for the analysis of the BCR-ABL gene.

Therefore, by improving the conventional methods, a detection method which may be more useful in diagnosing CML has been studied. As a result, a detection kit using a cleavable probe and a diagnosis method using the same according to the present invention were developed.

DETAILED DESCRIPTION OF THE INVENTION

Technical Problem

An embodiment of the present invention provides a kit for detecting a BCR-ABL fusion gene breakpoint, wherein the kit includes a primer set and a cleavable probe which enable to specifically amplify the BCR-ABL fusion gene breakpoint.

Another embodiment of the present invention provides a method of diagnosing chronic myelogenous leukemia, wherein the method uses a primer set and a cleavable probe which enable to specifically amplify a BCR-ABL fusion gene breakpoint.

Technical Solution

An aspect of the present invention provides a kit for detecting an e19a2 breakpoint of a BCR-ABL fusion gene, wherein the kit includes at least one primer set and a cleavable probe which enable to specifically amplify the e19a2 breakpoint of the BCR-ABL fusion gene.

An embodiment of the present invention provides a kit for detecting an e19a2 breakpoint of a BCR-ABL fusion gene, wherein the kit includes a first primer set including a primer including a nucleic acid of SEQ ID NO: 1 and a primer including a nucleic acid of SEQ ID NO: 2; and a cleavable probe of SEQ ID NO: 33.

Another embodiment of the present invention provides a kit for detecting an e19a2 breakpoint of a BCR-ABL fusion gene, wherein the kit includes a second primer set including a primer including a nucleic acid of SEQ ID NO: 3 and a primer including a nucleic acid of SEQ ID NO: 4; and a cleavable probe of SEQ ID NO: 33.

Another embodiment of the present invention provides a kit for detecting an e19a2 breakpoint of a BCR-ABL fusion gene, wherein the kit includes a third primer set including a primer including a nucleic acid of SEQ ID NO: 5 and a primer including a nucleic acid of SEQ ID NO: 6; and a cleavable probe of SEQ ID NO: 33.

Another embodiment of the present invention provides a kit for detecting an e19a2 breakpoint of a BCR-ABL fusion gene, wherein the kit includes a fourth primer set including a primer including a nucleic acid of SEQ ID NO: 7 and a primer including a nucleic acid of SEQ ID NO: 8; and a cleavable probe of SEQ ID NO: 33.

Another embodiment of the present invention provides a kit for detecting an e19a2 breakpoint of a BCR-ABL fusion gene, wherein the kit includes a fifth primer set including a primer including a nucleic acid of SEQ ID NO: 9 and a primer including a nucleic acid of SEQ ID NO: 10; and a cleavable probe of SEQ ID NO: 33.

The term "primer" used herein may be used interchangeably with "oligonucleotide" or "polynucleotide." The primer refers to an oligonucleotide which serves as a starting point to being DNA synthesis in PCR. A primer generally includes from about 15 to about 35 nucleotides and is hybridized with complementary regions of the target sequence.

The term "probe" used herein refers to an oligonucleotide which is specifically bound to a target sequence, and includes, for example, a polynucleotide including a specific region which is designed to be hybridized by a sequence-specific method with a complementary region of a specific nucleic acid sequence such as a target nucleic acid sequence. In one embodiment of the present invention, the oligonucleotide probe includes from about 15 to about 60 nucleotides. Appropriately, the oligonucleotide probe includes from about 18 to about 30 nucleotides.

The term "cleavable probe" used herein refers to a probe including two types of nucleic acid, for example, a DNA probe including some RNA nucleotides inside the DNA probe.

As the sequence of the cleavable probe, any sequence which may be complementarily bound to a sequence commonly existing in an amplification product which is amplified by using SEQ ID $NO_s$: 1 and 2, an amplification product which is amplified by using SEQ ID $NO_s$: 3 and 4, an amplification product which is amplified by using SEQ ID $NO_s$: 5 and 6, an amplification product which is amplified by using SEQ ID $NO_s$: 7 and 8, and an amplification product which is amplified by using SEQ ID $NO_s$: 9 and 10 may be used.

The cleavable probe may include an internal region in which from about one to about ten DNA nucleotides are substituted with RNA nucleotides, in which from about two to about eight DNA nucleotides are substituted with RNA nucleotides, or in which from about three to about seven DNA nucleotides are substituted with RNA nucleotides, but is not limited thereto. In addition, RNA nucleotides may be positioned inside a probe consecutively or non-consecutively. The cleavable probe may be a probe including a polynucleotide of SEQ ID NO: 33.

In addition, the cleavable probe may be labeled with a detectable material at both ends or inside of the probe. A mixture for PCR includes an RNase enzyme which may specifically cleave an RNA sequence part of an RNA-DNA double strand. After the cleavage by an RNase, all the fragments of a cleavable probe are dissociated from a target amplicon at a reaction temperature and dispersed in a reaction solution. As donors and acceptors labeled in the probe are separated, fluorescence emission by the donors may be monitored.

The term "label" or "detectable label" used herein refers to a fluorochrome compound which is bound to a probe by a covalent bond or a noncovalent bond, and may be a fluorescence resonance energy transfer (FRET) pair including a fluorescent donor and a fluorescent acceptor.

The term "fluorochrome" used herein refers to a fluorescent compound which emits light by being excited by light having a wavelength shorter than that of the emitted light. In addition, the term "fluorescent donor" refers to a fluorochrome which emits light measured by the assay disclosed in the present invention. In addition, a fluorescent donor may provide light which is absorbed by a fluorescent acceptor. The term "fluorescent acceptor" used herein refers to a secondary fluorochrome or a quencher which absorbs energy emitted from a fluorescent donor. A secondary fluorochrome absorbs energy emitted from a fluorescent donor and then emits light having a wavelength longer than that of the light emitted by a fluorescent donor. A quencher absorbs energy emitted from a fluorescent donor.

Any light-emitting molecules, appropriately, a fluorochrome and/or a quencher, may be used in an embodiment of the present invention. For example, the light-emitting molecule may be Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, fluorescein, Oregon Green 488, Oregon Green 514, tetramethyl rhodamine, rhodamine X, Texas Red dye, QSY 7, QSY33, Dabcyl, BODIPY FL, BODIPY 630/650, BODIPY6501665, BODIPY TMR-X, BODIPY TR-X, dialkylaminocoumarin, Cy3 (cyanine 3), Cy3.5, Cy5.5, Cy5, DTPA ($Eu^{3+}$)-AMCA, and TTHA ($Eu^{3+}$) AMCA, but is not limited thereto. Appropriately, a light-emitting molecule may be a FRET pair including 6-FAM and Iowa Black BQ, but is not limited thereto.

In addition, the kit for detecting c-Met gene may further include a thermostable polymerase or RNase, and enzymes included in the kit may be a thermostable polymerase and a thermostable RNase.

The term "thermostable" herein used and applied to an enzyme refers to an enzyme maintaining biological activity at an increased temperature (e.g., 55° C. or higher), or in a cycle in which heating and cooling are repeated. A thermostable polynucleotide polymerase may be used especially in a PCR amplification reaction. In an embodiment of the present invention, the thermostable polynucleotide polymerase may be Taq polymerase. The thermostable polynucleotide polymerase may be a Taq polymerase selected from the group consisting of AmpliTaq, AmpliTaq Stoffel fragment, SuperTaq, SuperTaq plus, LA Taq, LApro Taq, and EX Taq. In addition, the term "RNase" used herein refers to an enzyme specifically cleaving an RNA. The RNA may be a double-stranded RNA which may be a hybridized double-strand formed by hybridization of an RNA and a DNA.

In addition, the kit may be provided as a kit including a package unit having one or more reagents. The kit may include at least one selected from the group consisting of the following articles: a buffer, instruction, and a positive or negative control group. The kit may include containers of reagents which are mixed at an appropriate ratio to perform the method described herein. The regent containers appropriately include a unit number of reagent to omit measuring when the method is performed. In another embodiment of the present invention, the kit reagent further includes a reagent for extracting genome DNA or RNA from a biological sample. In addition, the kit reagent may include a reagent to be applied to a reverse transcriptase-PCR analysis.

The kit for detecting an e19a2 breakpoint of a BCR-ABL fusion gene may include one primer set selected from the group consisting of the first to fifth primer sets to identify the e19a2 breakpoint, but include all the five primer sets to increase the accuracy.

Another aspect of the present invention provides a kit for detecting an e13a2, e14a2, e13a3, or e14a3 breakpoint of a BCR-ABL fusion gene, wherein the kit includes a primer set and a cleavable probe which enable to specifically amplify the e13a2, e14a2, e13a3, or e14a3 breakpoint of the BCR-ABL fusion gene.

One embodiment of the present invention provides a kit for detecting an e13a2, e14a2, e13a3, or e14a3 breakpoint of a BCR-ABL fusion gene, wherein the kit includes a sixth primer set including a primer including a nucleic acid of SEQ ID NO: 11 and a primer including a nucleic acid of SEQ ID NO: 12; and a cleavable probe of SEQ ID NO: 33.

One embodiment of the present invention provides a kit for detecting an e13a2, e14a2, e13a3, or e14a3 breakpoint of a BCR-ABL fusion gene, wherein the kit includes a seventh primer set including a primer including a nucleic acid of SEQ ID NO: 13 and a primer including a nucleic acid of SEQ ID NO: 14; and a cleavable probe of SEQ ID NO: 33.

One embodiment of the present invention provides a kit for detecting an e13a2, e14a2, e13a3, or e14a3 breakpoint of a BCR-ABL fusion gene, wherein the kit includes an eighth primer set including a primer including a nucleic acid of SEQ ID NO: 15 and a primer including a nucleic acid of SEQ ID NO: 16; and a cleavable probe of SEQ ID NO: 33.

One embodiment of the present invention provides a kit for detecting an e13a2, e14a2, e13a3, or e14a3 breakpoint of a BCR-ABL fusion gene, wherein the kit includes a ninth primer set including a primer including a nucleic acid of SEQ ID NO: 17 and a primer including a nucleic acid of SEQ ID NO: 18; and a cleavable probe of SEQ ID NO: 33.

One embodiment of the present invention provides a kit for detecting an e13a2, e14a2, e13a3, or e14a3 breakpoint of a BCR-ABL fusion gene, wherein the kit includes a tenth primer set including a primer including a nucleic acid of SEQ ID NO: 19 and a primer including a nucleic acid of SEQ ID NO: 20; and a cleavable probe of SEQ ID NO: 33.

One embodiment of the present invention provides a kit for detecting an e13a2, e14a2, e13a3, or e14a3 breakpoint of a BCR-ABL fusion gene, wherein the kit includes an eleventh primer set including a primer including a nucleic acid of SEQ ID NO: 21 and a primer including a nucleic acid of SEQ ID NO: 22; and a cleavable probe of SEQ ID NO: 33.

The kit for detecting an e13a2, e14a2, e13a3, or e14a3 breakpoint of a BCR-ABL fusion gene may include one primer set selected from the group consisting of the sixth to eleventh primer sets to identify the breakpoint, but include all the six primer sets to increase the accuracy.

As the sequence of the cleavable probe, any sequence which may be complementarily bound to a sequence commonly existing in an amplification product which is amplified by using SEQ ID $NO_s$: 11 and 12, an amplification product which is amplified by using SEQ ID $NO_s$: 13 and 14, an amplification product which is amplified by using SEQ ID $NO_s$: 15 and 16, an amplification product which is amplified by using SEQ ID $NO_s$: 17 and 18, an amplification product which is amplified by using SEQ ID $NO_s$: 19 and 20, and an amplification product which is amplified by using SEQ ID $NO_s$: 21 and 22 may be used. The cleavable probe may be a probe including a polynucleotide of SEQ ID NO: 33.

Another aspect of the present invention provides a kit for detecting an e1a2 breakpoint of a BCR-ABL fusion gene, wherein the kit includes a primer set and a cleavable probe which enable to specifically amplify the e1a2 breakpoint of the BCR-ABL fusion gene.

An embodiment of the present invention provides a kit for detecting an e1a2 breakpoint of a BCR-ABL fusion gene, wherein the kit includes a twelfth primer set including a primer including a nucleic acid of SEQ ID NO: 23 and a primer including a nucleic acid of SEQ ID NO: 24; and a cleavable probe of SEQ ID NO: 33, Another embodiment of the present invention provides a kit for detecting an e1a2 breakpoint of a BCR-ABL fusion gene, wherein the kit includes a thirteenth primer set including a primer including a nucleic acid of SEQ ID NO: 25 and a primer including a nucleic acid of SEQ ID NO: 26; and a cleavable probe of SEQ ID NO: 33.

Another embodiment of the present invention provides a kit for detecting an e1a2 breakpoint of a BCR-ABL fusion gene, wherein the kit includes a fourteenth primer set including a primer including a nucleic acid of SEQ ID NO: 27 and a primer including a nucleic acid of SEQ ID NO: 28; and a cleavable probe of SEQ ID NO: 33.

Another embodiment of the present invention provides a kit for detecting an e1a2 breakpoint of a BCR-ABL fusion gene, wherein the kit includes a fifteenth primer set including a primer including a nucleic acid of SEQ ID NO: 29 and a primer including a nucleic acid of SEQ ID NO: 30; and a cleavable probe of SEQ ID NO: 33.

Another embodiment of the present invention provides a kit for detecting an e1a2 breakpoint of a BCR-ABL fusion gene, wherein the kit includes a sixteenth primer set including a primer including a nucleic acid of SEQ ID NO: 31 and a primer including a nucleic acid of SEQ ID NO: 32; and a cleavable probe of SEQ ID NO: 33.

The kit for detecting an e1a2 breakpoint of a BCR-ABL fusion gene may include one primer set selected from the group consisting of the twelfth to sixteenth primer sets to identify the e1a2 breakpoint, but include all the five primer sets to increase the accuracy.

As the sequence of the cleavable probe, any sequence which may be complementarily bound to a sequence commonly existing in an amplification product which is amplified by using SEQ ID $NO_s$: 23 and 24, an amplification product which is amplified by using SEQ ID $NO_s$: 25 and 26, an amplification product which is amplified by using SEQ ID $NO_s$: 27 and 28, an amplification product which is amplified by using SEQ ID $NO_s$: 29 and 30, and an amplification product which is amplified by using SEQ ID $NO_s$: 30 and 31 may be used. The cleavable probe may be a probe including a polynucleotide of SEQ ID NO: 33.

Another aspect of the present invention provides a multiplex kit for detecting a CML gene, wherein the kit includes the first to sixteenth primer sets and a cleavable probe.

To detect CML, one primer set selected from the group consisting of the first to sixteenth primer sets may be used. However, CML has various breakpoints, since translocation occurs at various regions in CML. Therefore, for a more accurate detection, a kit for detecting a CML gene may include all the primer sets including the primer set enabling to detect the e19a2 breakpoint, the primer set enabling to detect the e13a2, e14a2, e13a3, or e14a3 breakpoint, and the primer set enabling to detect the e1a2 breakpoint. In other words, a kit for detecting a CML gene may appropriately include one primer set selected from the group consisting of the first to fifth primer sets, one primer set selected from the group consisting of the sixth to eleventh primer sets, and one primer set selected from the group consisting of the twelfth to sixteenth primer sets.

In addition, the cleavable probe enables to amplify a CML gene is not limited a specific sequence so long as the sequence may be specifically bound to an amplification product produced by the primer sets. The cleavable probe may be a probe including a polynucleotide of SEQ ID NO: 33.

The primer set may further include a thermostable polymerase or an RNase.

Another aspect of the present invention provides a multiplex method of detecting a CML gene by using the kit for detecting a CML gene, wherein the kit includes the first to sixteenth primer sets and a cleavable probe.

One embodiment of the present invention provides a multiplex method of detecting a CML gene including obtaining DNA from a sample; mixing at least one primer set, a cleavable probe of SEQ ID NO: 33, and the obtained DNA sample to prepare a mixed sample, wherein the at least one primer set is selected from the group consisting of a first primer set including a primer including a nucleic acid of SEQ ID NO: 1 and a primer including a nucleic acid of SEQ ID NO: 2; a second primer set including a primer including a nucleic acid of SEQ ID NO: 3 and a primer including a nucleic acid of SEQ ID NO: 4; a third primer set including a primer including a nucleic acid of SEQ ID NO: 5 and a primer including a nucleic acid of SEQ ID NO: 6; a fourth primer set including a primer including a nucleic acid of SEQ ID NO: 7 and a primer including a nucleic acid of SEQ ID NO: 8; a fifth primer set including a primer including a nucleic acid of SEQ ID NO: 9 and a primer including a nucleic acid of SEQ ID NO: 10; a sixth primer set including a primer including a nucleic acid of SEQ ID NO: 11 and a primer including a nucleic acid of SEQ ID NO: 12; a seventh primer set including a primer including a nucleic acid of SEQ ID NO: 13 and a primer including a nucleic acid of SEQ ID NO: 14; an eighth primer set including a primer including a nucleic acid of SEQ ID NO: 15 and a primer including a nucleic acid of SEQ ID NO: 16; a ninth primer set including a primer including a nucleic acid of SEQ ID NO: 17 and a primer including a nucleic acid of SEQ ID NO: 18; a tenth primer set including a primer including a nucleic acid of SEQ ID NO: 19 and a primer including a nucleic acid of SEQ ID NO: 20; an eleventh primer set including a primer including a nucleic acid of SEQ ID NO: 21 and a primer including a nucleic acid of SEQ ID NO; 22; a twelfth primer set including a primer including a nucleic acid of SEQ ID NO: 23 and a primer including a nucleic acid of SEQ ID NO: 24; a thirteenth primer set including a primer including a nucleic acid of SEQ ID NO: 25 and a primer including a nucleic acid of SEQ ID NO: 26; a fourteenth primer set including a primer including a nucleic acid of SEQ ID NO: 27 and a primer including a nucleic acid of SEQ ID NO: 28; a fifteenth primer set including a primer including a nucleic acid of SEQ ID NO: 29 and a primer including a nucleic acid of SEQ ID NO: 30; and a sixteenth primer set including a primer including a nucleic acid of SEQ ID NO: 31 and a primer including a nucleic acid of SEQ ID NO: 32; mixing a polymerase, an RNase, and an amplification buffer with the mixed sample to amplify the DNA; and detecting an increase of a signal emitted from a label on the probe.

The multiplex method of detecting a CML gene is described below in detail.

First, the multiplex method of detecting a CML gene may include obtaining DNA from a sample. The sample may be obtained from a CML patient and a person who wants to undergo diagnosis of CML progress. In addition, the sample may be directly taken from a specific body part.

Subsequently, the multiplex method of detecting a CML gene may include mixing at least one primer set, a cleavable probe of SEQ ID NO: 33, and the obtained DNA sample to prepare a mixed sample, wherein the at least one primer set is selected from the group consisting of a first primer set including a primer including a nucleic acid of SEQ ID NO: 1 and a primer including a nucleic acid of SEQ ID NO: 2; a second primer set including a primer including a nucleic acid of SEQ ID NO: 3 and a primer including a nucleic acid of SEQ ID NO: 4; a third primer set including a primer including a nucleic acid of SEQ ID NO: 5 and a primer including a nucleic acid of SEQ ID NO: 6; a fourth primer set including a primer including a nucleic acid of SEQ ID NO: 7 and a primer including a nucleic acid of SEQ ID NO: 8; a fifth primer set including a primer including a nucleic acid of SEQ ID NO: 9 and a primer including a nucleic acid of SEQ ID NO: 10; a sixth primer set including a primer including a nucleic acid of SEQ ID NO: 11 and a primer including a nucleic acid of SEQ ID NO: 12; a seventh primer set including a primer including a nucleic acid of SEQ ID NO: 13 and a primer including a nucleic acid of SEQ ID NO: 14; an eighth primer set including a primer including a nucleic acid of SEQ ID NO: 15 and a primer including a nucleic acid of SEQ ID NO: 16; a ninth primer set including a primer including a nucleic acid of SEQ ID NO: 17 and a primer including a nucleic acid of SEQ ID NO: 18; a tenth primer set including a primer including a nucleic acid of SEQ ID NO: 19 and a primer including a nucleic acid of SEQ ID NO: 20; an eleventh primer set including a primer including a nucleic acid of SEQ ID NO: 21 and a primer including a nucleic acid of SEQ ID NO: 22; a twelfth primer set including a primer including a nucleic acid of SEQ ID NO: 23 and a primer including a nucleic acid of SEQ ID NO: 24; a thirteenth primer set including a primer including a nucleic acid of SEQ ID NO: 25 and a primer including a nucleic acid of SEQ ID NO: 26; a fourteenth primer set including a primer including a nucleic acid of SEQ ID NO: 27 and a primer including a nucleic acid of SEQ ID NO: 28; a fifteenth primer set including a primer including a nucleic acid of SEQ ID NO: 29 and a primer including a nucleic acid of SEQ ID NO: 30; and a sixteenth primer set including a primer including a nucleic acid of SEQ ID NO: 31 and a primer including a nucleic acid of SEQ ID NO: 32 with a cleavable of SEQ ID NO: 33 and the obtained DNA sample.

Two or more primer sets selected from the group consisting of the first to sixteenth primer sets may be used. In addition, all the sixteen primer sets may be used simultaneously.

The cleavable probe may be labeled with a detectable material at both ends of different DNA parts. The cleavable probe may be labeled with a fluorescence resonance energy transfer (FRET) pair including a fluorescent donor and a fluorescent acceptor.

Subsequently, the multiplex method of detecting a CML gene may include mixing a polymerase, an RNase, and an amplification buffer with the mixed sample to amplify the DNA. Any thermostable polymerase or a RNase may be used.

The term "amplification buffer" refers to a compound which is added to an amplification reaction to control the amplification reaction and thereby modify the stability, activity, and/or lifecycle of at least one element of the amplification reaction. The buffer may be compatible with PCR amplification and RNase H cleavage activity. Examples of the buffer include a buffer including 4-(2-hydroxyethyl)-1-piperazine ethane sulfonic acid (HEPES), 3-(N-morpholino) propane sulfonic acid (MOPS), acetate or phosphate, but are not limited thereto.

A PCR buffer may generally include about 70 mM or lower KCl, about 1.5 mM or higher MgCl$_2$, and from about 50 to about 200 μM of each dATP, dCTP, dGTP and dTTP. The buffer may further include an additive for an efficient reverse transcriptase PCR or to optimize a PCR.

An additive is a compound which is added to modify the stability, activity, and/or lifecycle of at least one element of the composition. Examples of the additive include betaine, formamide, KCl, CaCl$_2$, MgOAc, MgCl$_2$, NaCl, NH$_4$OAc, NaI, Na(CO$_3$)$_2$, LiCl, MnOAc, NMP, trehalose, Demethyl sulfoxide (DMSO), glycerol, ethylene glycol, dithiothreitol (DTT), pyrophosphatase, inorganic pyrophosphatase (TAP), a cation, and other compounds, proteins, or cofactors which may modify the amplification efficiency, but are not limited thereto. An additive may be selectively added to improve selectivity of primer annealing.

Subsequently, the multiplex method of detecting a CML gene may include detecting an increase of a signal emitted from a label on the probe. The emitted signal may be fluorescence. The result of fluorescence emission may be detected by using an appropriate device such as Applied Biosystems 7500 Fast Real-Time PCR System or Biorad CFX96 real-time PCR thermocycler, but all devices available in the art may be used.

Additionally, the multiplex method of detecting a CML gene may include a reverse transcription PCR in which an RNA is obtained from a sample and amplified the RNA by using a reverse transcriptase to provide the resulting cDNA as a sample DNA. An RNA may be taken from a CML patient or a person who wants to undergo CML diagnosis, and then the RNA may be amplified by using a reverse transcriptase to obtain a cDNA. Reverse transcription to a cDNA by using a reverse transcriptase may be performed by any methods available in the art.

In the reverse transcriptase PCR, a template-specific DNA primer is used to produce a complementary DNA strand. Then, in a PCR, the product is modified, and a second template-specific primer is bound to the cDNA and is extended to form a duplex DNA. The resulting product is amplified in the next temperature cycle. To maintain the highest sensitivity, it is important to prevent the RNA from being degraded before cDNA synthesis.

Advantageous Effects

When the primer set and the cleavable probe according to one embodiment of the present invention, wherein the primer set and the cleavable probe are specifically bound to a chronic myelogenous leukemia (CML) gene, are used, a very little amount of expression of the gene including a breakpoint which causes CLM may be detected, and thus CML related with CML gene expression may be diagnosed and the prognosis may be easily determined.

EXAMPLES

Figure 1:
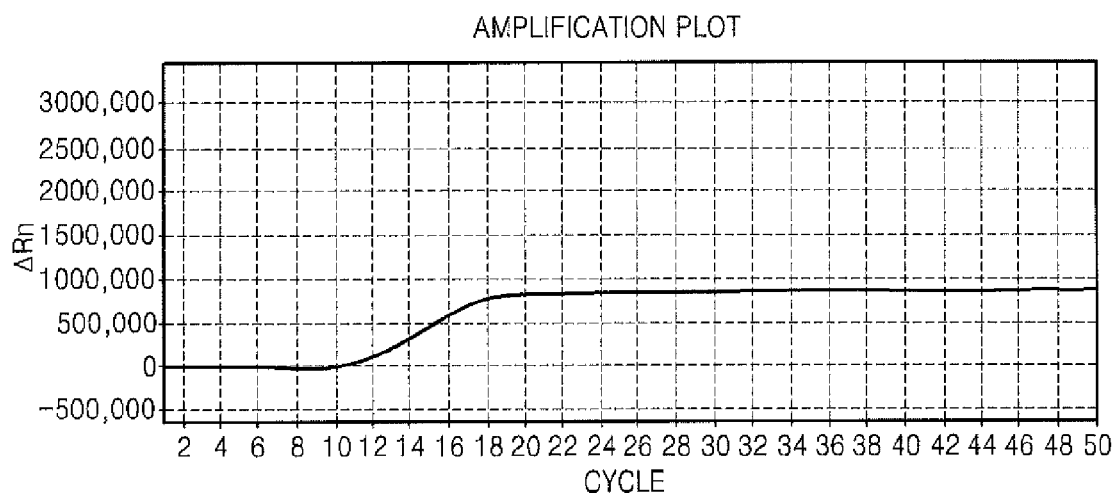
FIGS. 1 to 5 show the experimental results of amplifying the e19a2 target nucleotide sequence by using the primer set no. of 1-5.

Hereinafter, the present invention is described in more detail with reference to the examples below. However, these examples are for illustrative purposes only and are not intended to limit the scope of the invention.

Example 1

Preparation of Primer Set and Probe for CML Detection

A total of 16 sets of primers set (F: forward primer, R: reverse primer) and a probe for CML detection (The nucleotide represented as a small letter is RNA.) were prepared (synthesized by Integrated DNA Technologies, Inc.).

The CataCleave probe is the same: 5'-ggggaatggtgugaagcccaaacc-3' (SEQ ID NO: 33) (Nucleotides underlined are RNA.)

The primer set for detecting R-ABL e19a2 (F: forward primer, R: reverse primer).

TABLE 1

| Set no. | | ID sequences | SEQ ID NO | Binding site | Length (bp) |
|---|---|---|---|---|---|
| 1 | F | gaggtgggcatctaccgcgt | SEQ ID NO: 1 | BCR-e19 | 20 |
|   | R | gctgccattgatcccgctgc | SEQ ID NO: 2 | ABL-a3 | 20 |
| 2 | F | tctaccgcgtgtccggtgtg | SEQ ID NO: 3 | BCR-e19 | 20 |
|   | R | gctgccattgatcccgctgc | SEQ ID NO: 4 | ABL-a3 | 20 |
| 3 | F | tgcgtggaggagatcgagcg | SEQ ID NO: 5 | BCR-e19 | 20 |
|   | R | gctgccattgatcccgctgc | SEQ ID NO: 6 | ABL-a3 | 20 |
| 4 | F | aggtgggcatctaccgcgtg | SEQ ID NO: 7 | BCR-e19 | 20 |
|   | R | gctgccattgatcccgctgc | SEQ ID NO: 8 | ABL-a3 | 20 |
| 5 | F | tgcgtggaggagatcgagcg | SEQ ID NO: 9 | BCR-e19 | 20 |
|   | R | attgcgggacacaggcccat | SEQ ID NO: 10 | ABL-a3 | 20 |

The primer set for detecting BCR-ABL e13a2 (=b2a2), e14a2 (=b3a2), e13a3 (=b2a3), e14a3 (=b3a3) (F: forward primer, R: reverse primer).

TABLE 2

| Set no. | | ID sequences | SEQ ID NO | Binding site | Length (bp) |
|---|---|---|---|---|---|
| 6 | F | agcttctccctgacatcc gtggag | SEQ ID NO: 11 | BCR-e13 | 24 |
|   | R | attgcgggacacaggcccat | SEQ ID NO: 12 | ABL-a3 | 20 |
| 7 | F | ctgcagatgctgaccaact cgtgt | SEQ ID NO: 13 | BCR-e13 | 24 |
|   | R | attgcgggacacaggcccat | SEQ ID NO: 14 | ABL-a3 | 20 |
| 8 | F | gatgctgaccaactcgtgtgt gaaac | SEQ ID NO: 15 | BCR-e13 | 26 |
|   | R | cattgcgggacacaggcccat | SEQ ID NO: 16 | ABL-a3 | 20 |
| 9 | F | agcttctccctgacatccg tggag | SEQ ID NO: 17 | BCR-e13 | 24 |
|   | R | gctgccattgatcccgctgc | SEQ ID NO: 18 | ABL-a3 | 20 |
| 10 | F | ctgcagatgctgaccaac tcgtgt | SEQ ID NO: 19 | BCR-e13 | 24 |
|   | R | gctgccattgatcccgctgc | SEQ ID NO: 20 | ABL-a3 | 20 |
| 11 | F | gatgctgaccaactcgtgtg tgaaac | SEQ ID NO: 21 | BCR-e13 | 26 |
|   | R | gctgccattgatcccgctgc | SEQ ID NO: 22 | ABL-a3 | 20 |

The primer set for detecting BCR-ABL e1a2 (F: forward primer, R: reverse primer).

TABLE 3

| Set no. | | ID sequences | SEQ ID NO | Binding site | Length (bp) |
|---|---|---|---|---|---|
| 12 | F | cataagcggcaccggcactg | SEQ ID NO: 23 | BCR-e1 | 20 |
|    | R | attgcgggacacaggcccat | SEQ ID NO: 24 | ABL-a3 | 20 |
| 13 | F | actgcccggttgtcgtgtcc | SEQ ID NO: 25 | BCR-e1 | 20 |
|    | R | attgcgggacacaggcccat | SEQ ID NO: 26 | ABL-a3 | 20 |
| 14 | F | cactgcccggttgtcgtgtc | SEQ ID NO: 27 | BCR-e1 | 20 |
|    | R | gctgccattgatcccgctgc | SEQ ID NO: 28 | ABL-a3 | 20 |
| 15 | F | ccataagcggcaccggcact | SEQ ID NO: 29 | BCR-e1 | 20 |
|    | R | attgcgggacacaggcccat | SEQ ID NO: 30 | ABL-a3 | 20 |
| 16 | F | cccggttgtcgtgtccgagg | SEQ ID NO: 31 | BCR-e1 | 20 |
|    | R | gctgccattgatcccgctgc | SEQ ID NO: 32 | ABL-a3 | 20 |

In addition, the two DNA ends of the CataCleave probe, which is a cleavable probe, were labeled by using 6-FAM, which is a fluorochrome, at the 5'-end and Iowa Black RQ, which is a quencher, at the 3'-end.

Example 2

Sampling

To prepare a positive BCR-ABL sample, plasmids (six plasmids: one plasmid per one genotype) synthesized by gene cloning were prepared (Refer to SEQ ID NOs: 34 to 39). A polynucleotide encoding the gene sequence listed below was inserted to the EcoR1/BamH1 site of pGEM-3Z (Promega) to prepare a positive sample.

TABLE 4

| SEQ ID NO | Genotype |
|---|---|
| SEQ ID NO: 34 | e14a2 |
| SEQ ID NO: 35 | e13a2 |
| SEQ ID NO: 36 | e14a3 |
| SEQ ID NO: 37 | e13a3 |
| SEQ ID NO: 38 | e1a2 |
| SEQ ID NO: 39 | e19a2 |

Example 3

CML Gene Detection

Figure 2:
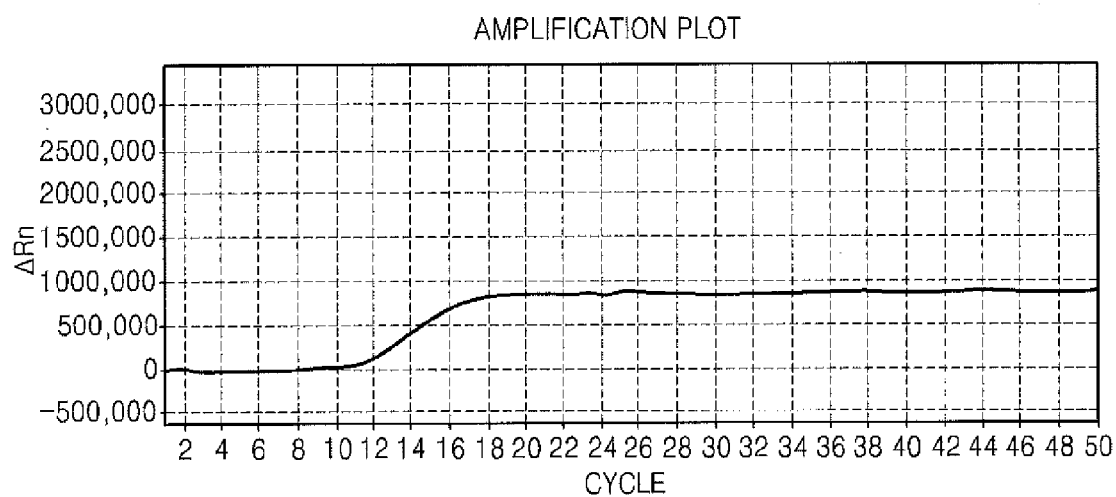
Figure 3:
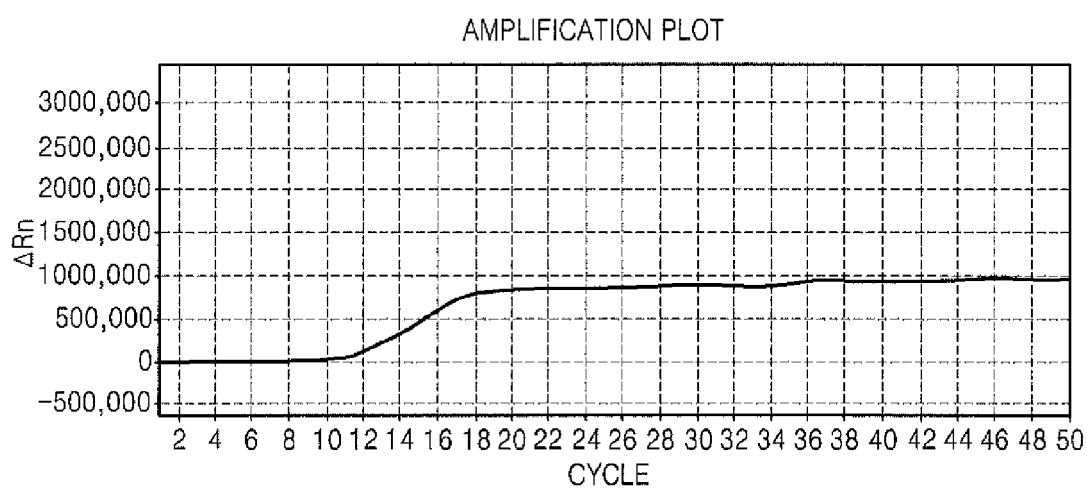
Figure 4:
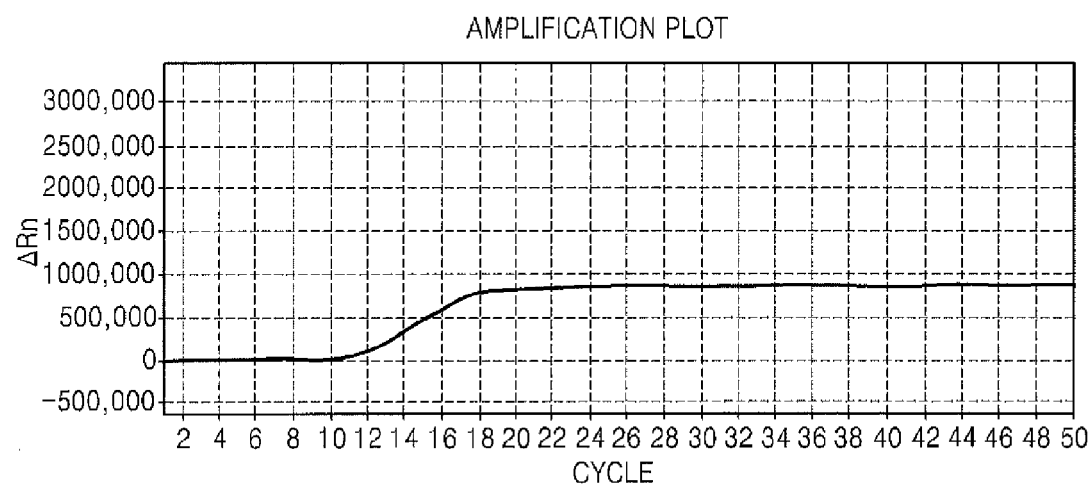
Figure 5:
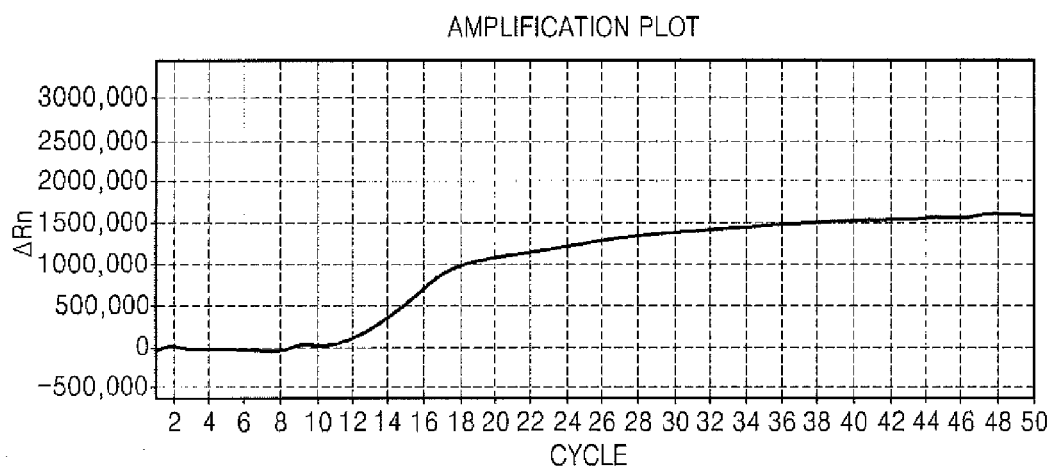
Figure 6:
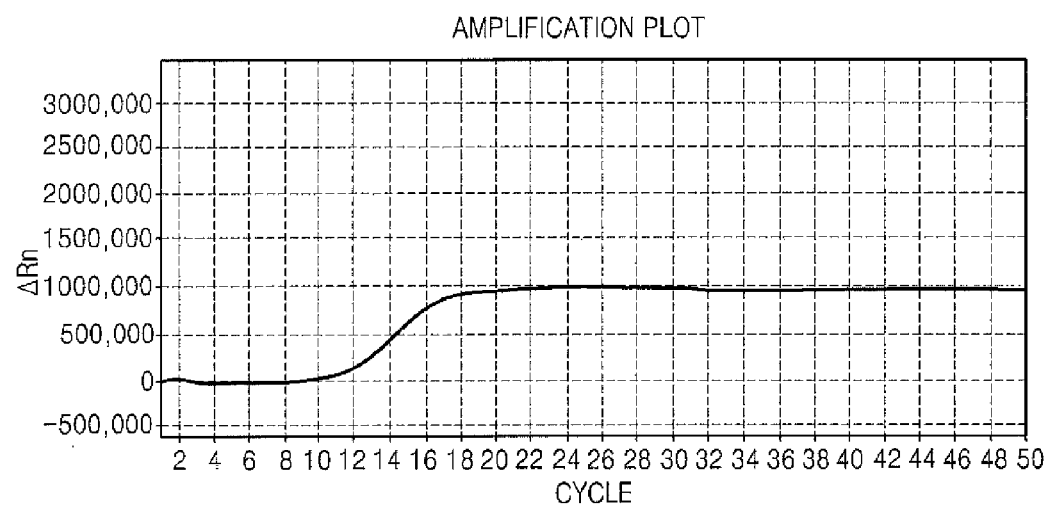
FIGS. 6 to 11 show the experimental results of amplifying the e14a2 target nucleotide sequence by using primer set no. of 6-11.
Figure 7:
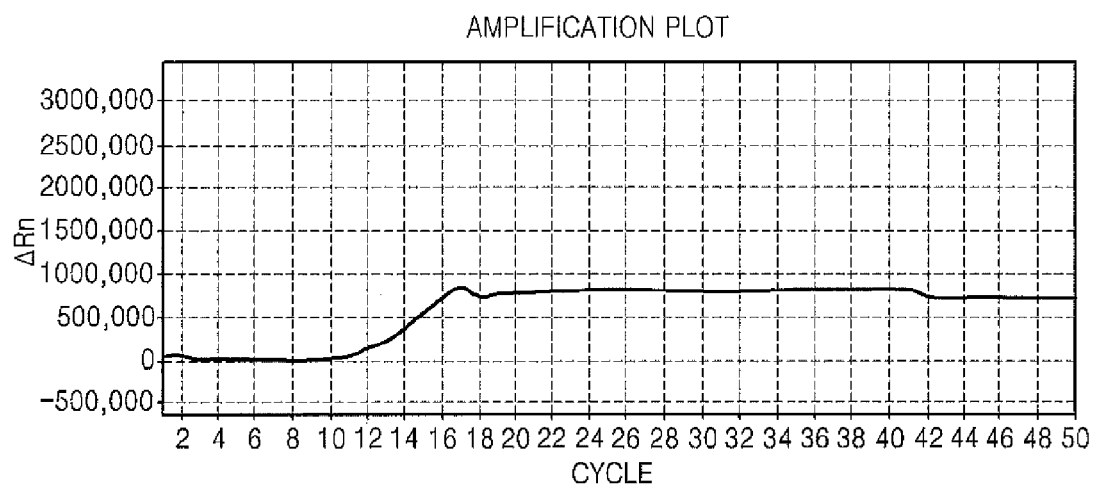
Figure 8:
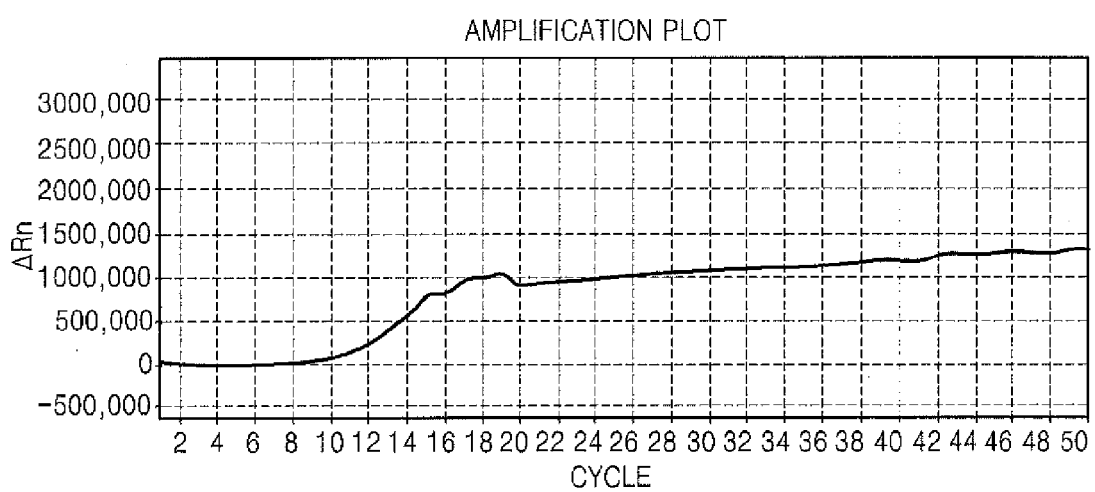
Figure 9:
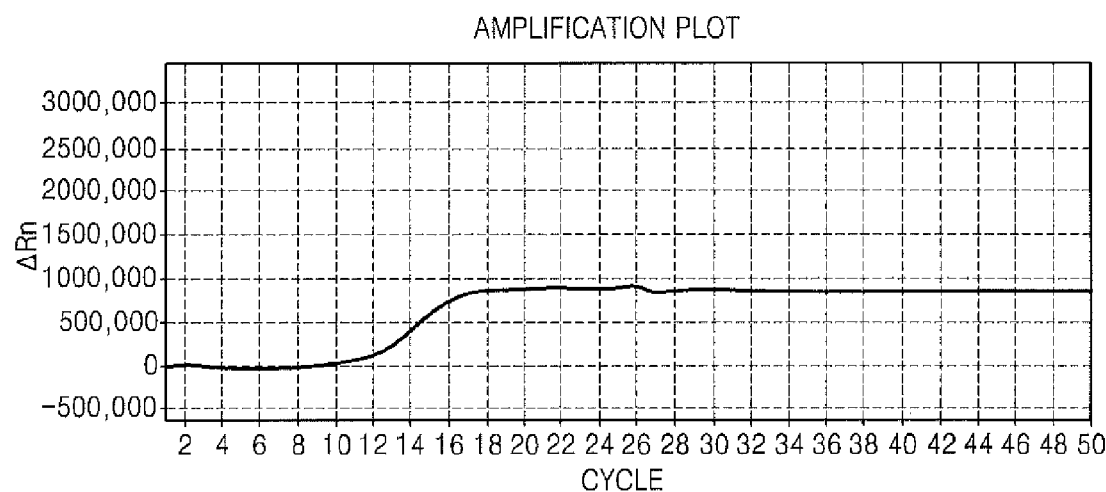
Figure 10:
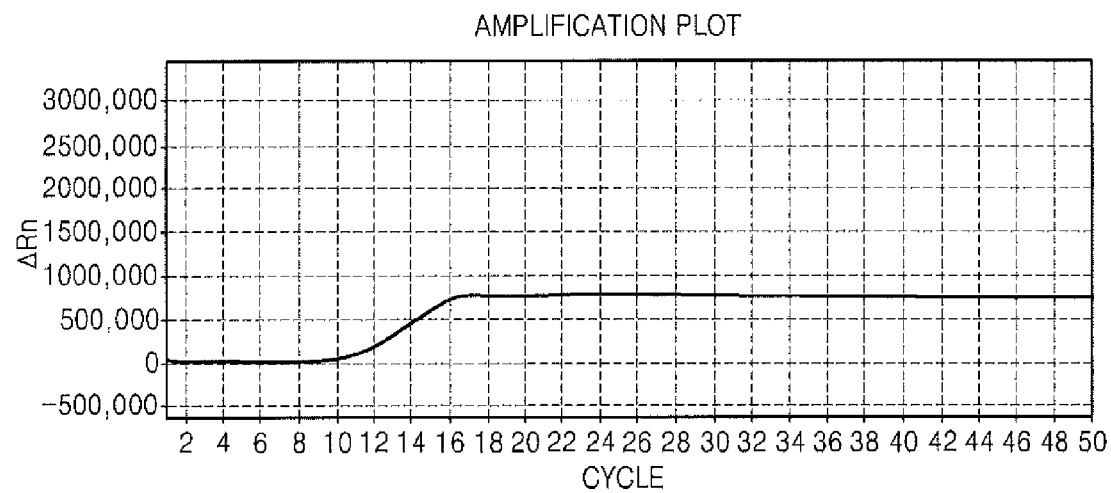
Figure 11:
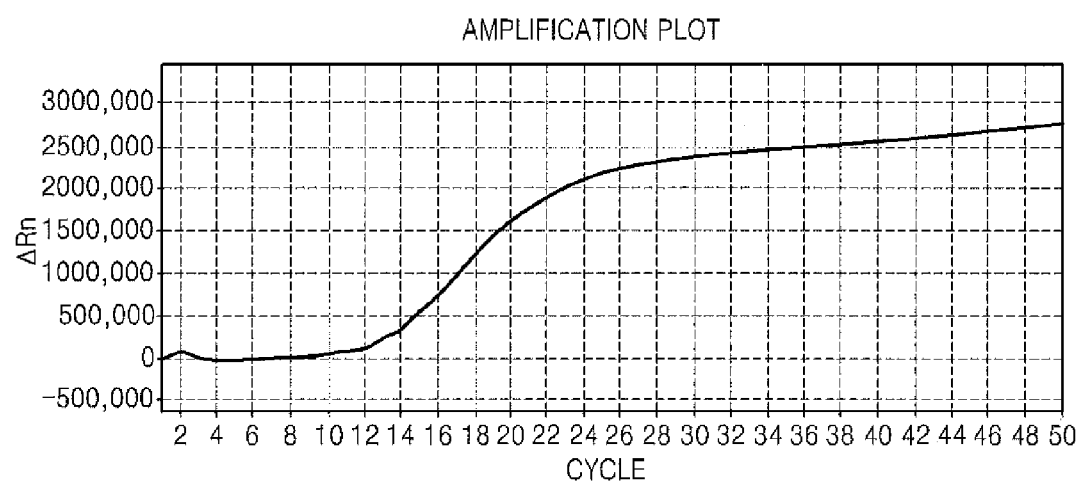
Figure 12:
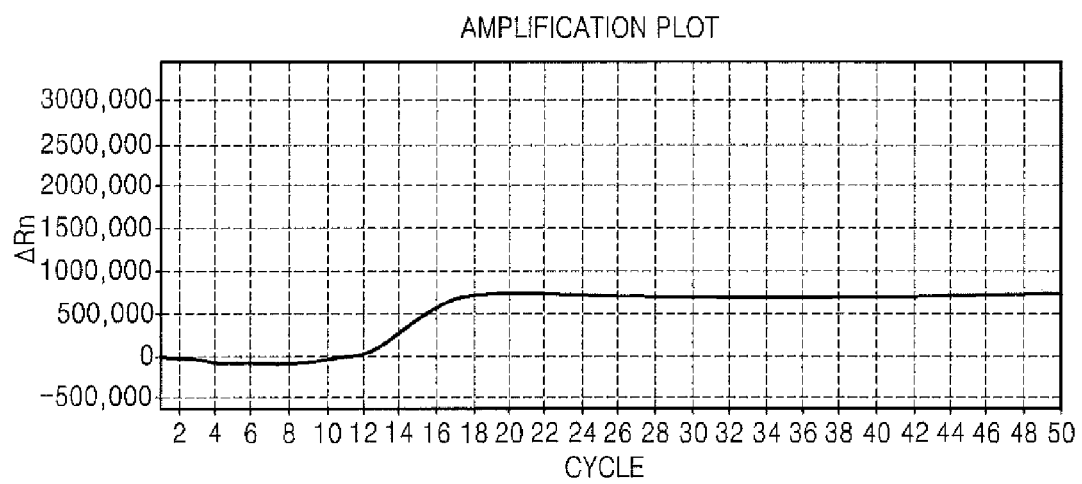
FIGS. 12 to 17 show the experimental results of amplifying the e13a2 target nucleotide sequence by using the primer set no. of 6-11.
Figure 13:
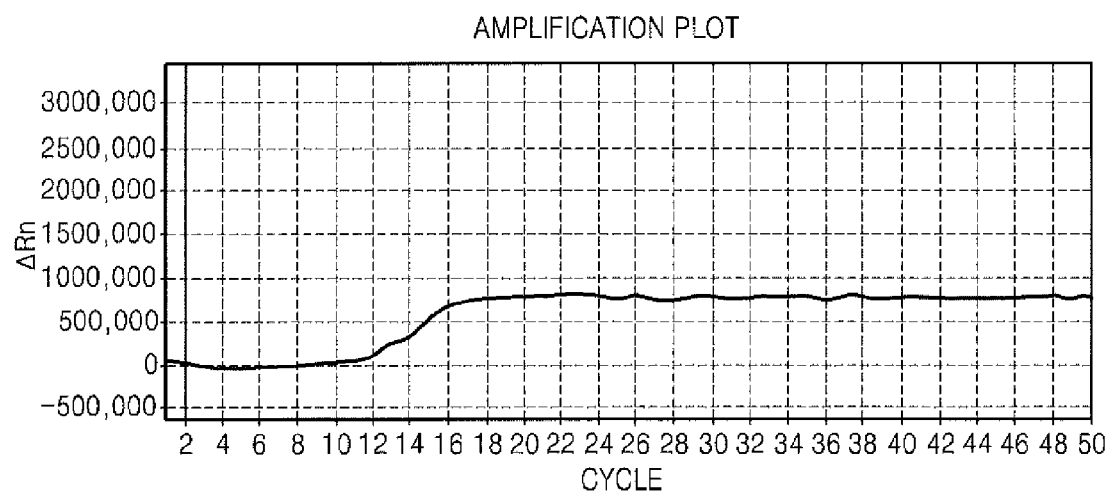
Figure 14:
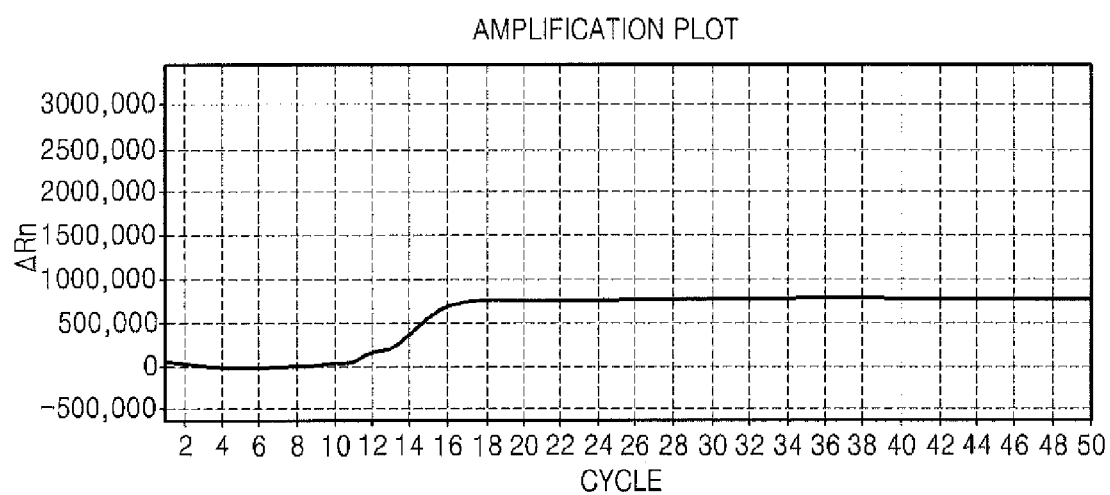
Figure 15:
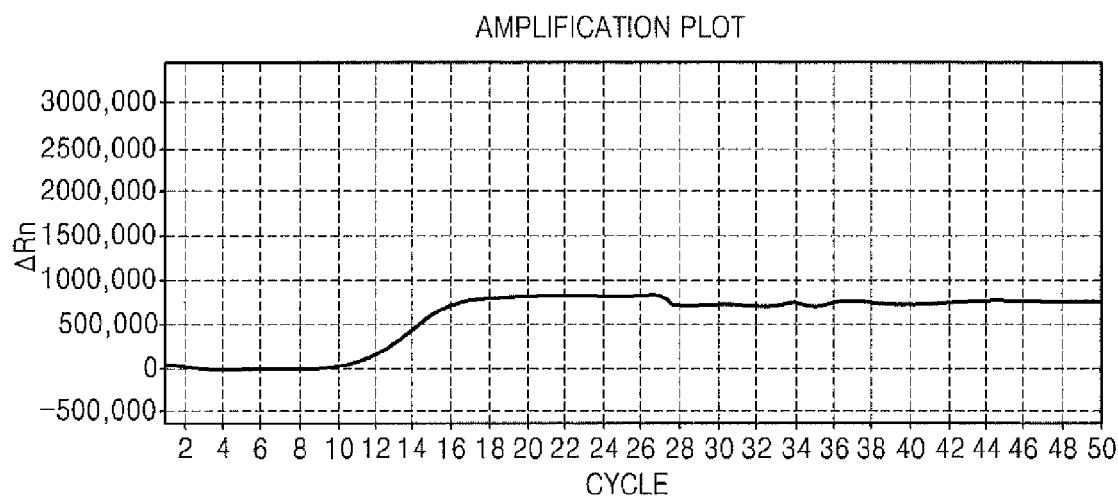
Figure 16:
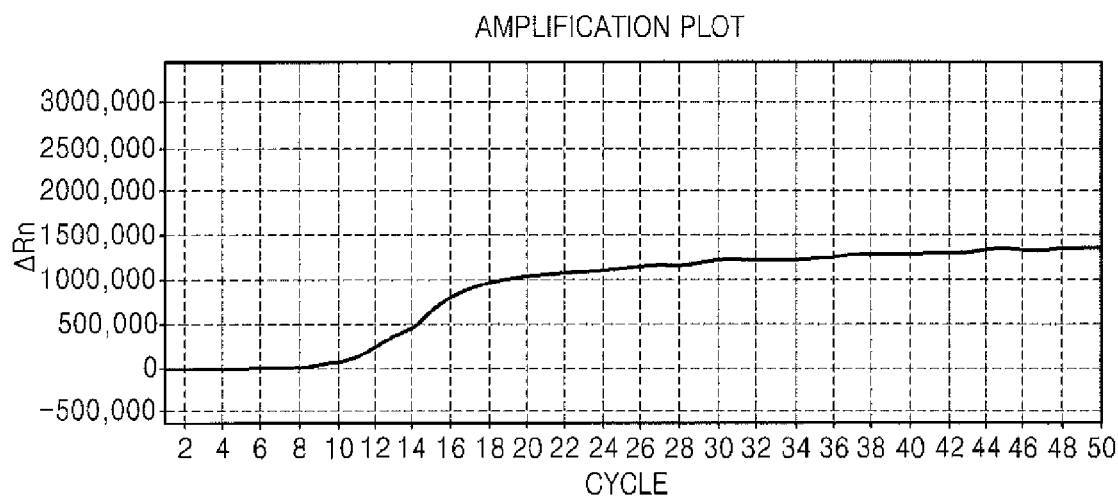
Figure 17:
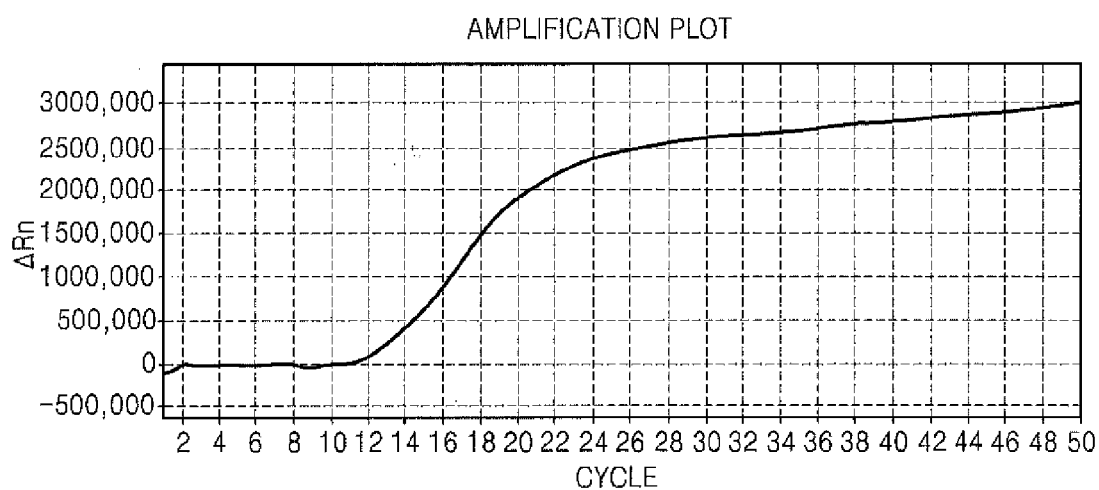
Figure 18:
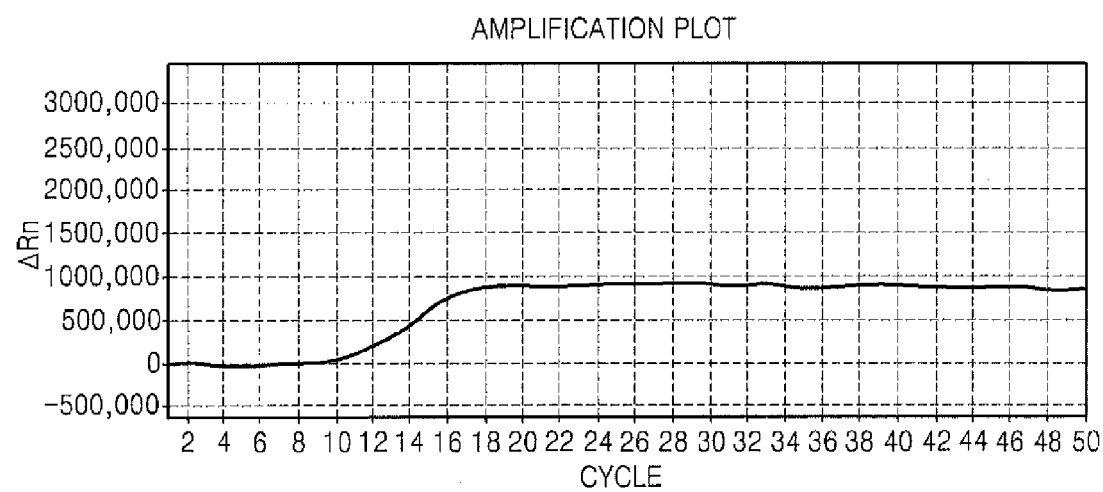
FIGS. 18 to 23 show the experimental results of amplifying the e14a3 target nucleotide sequence by using the primer set no. of 6-11.
Figure 19:
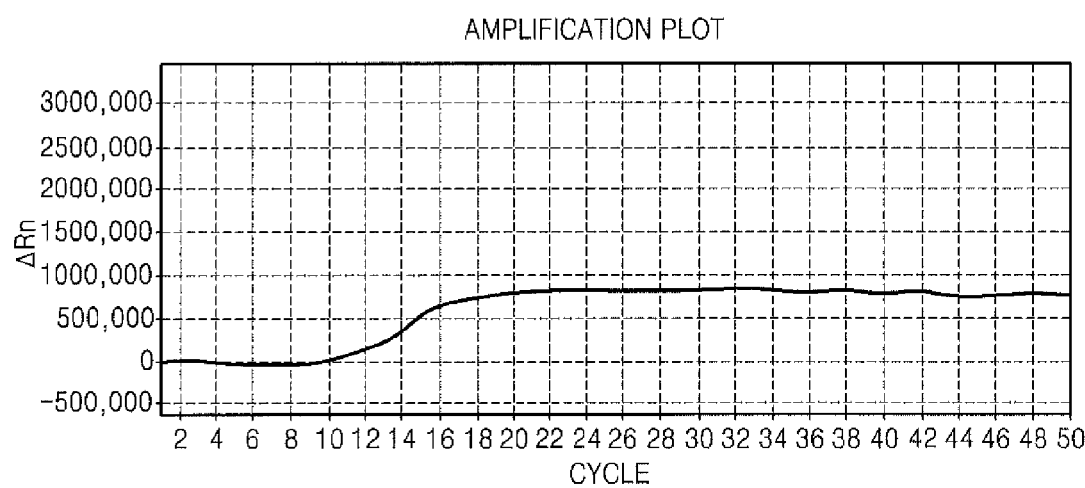
Figure 20:
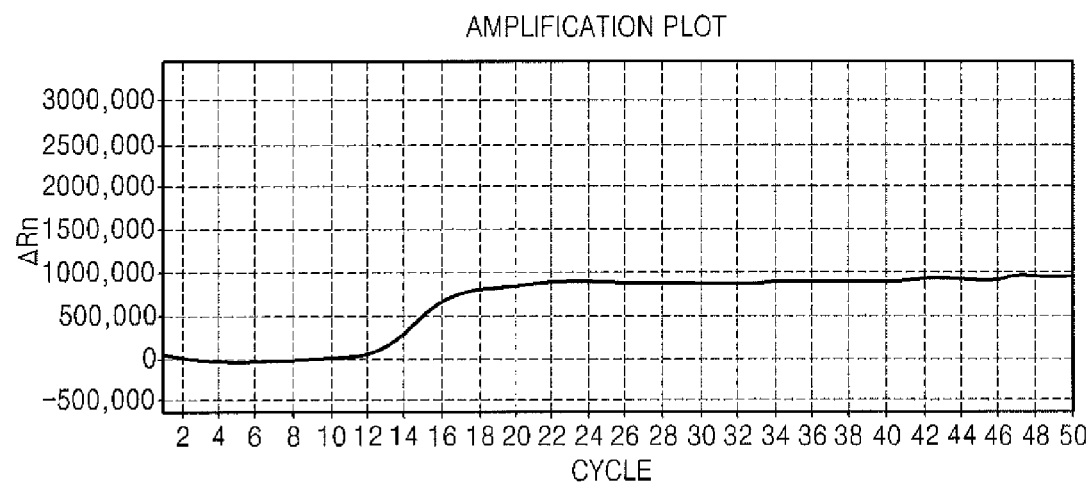
Figure 21:
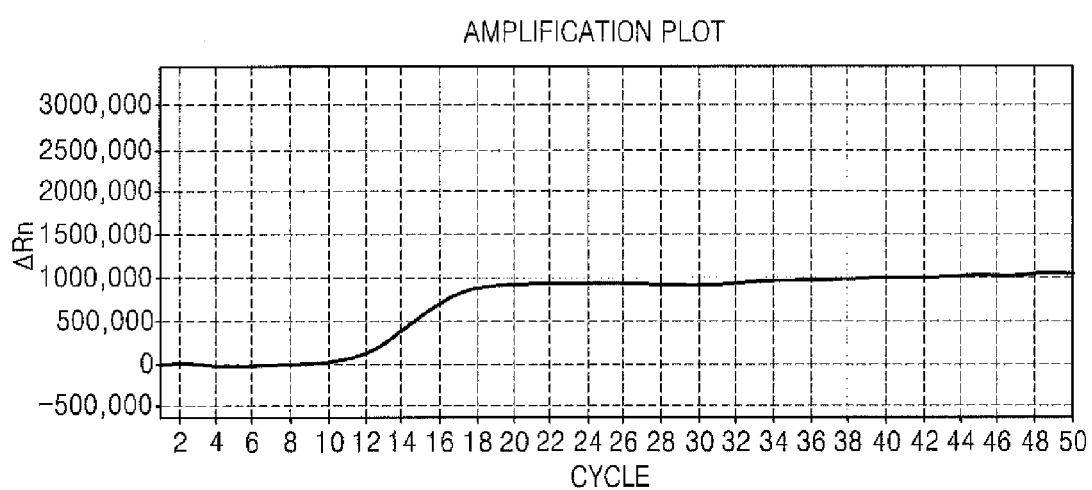
Figure 22:
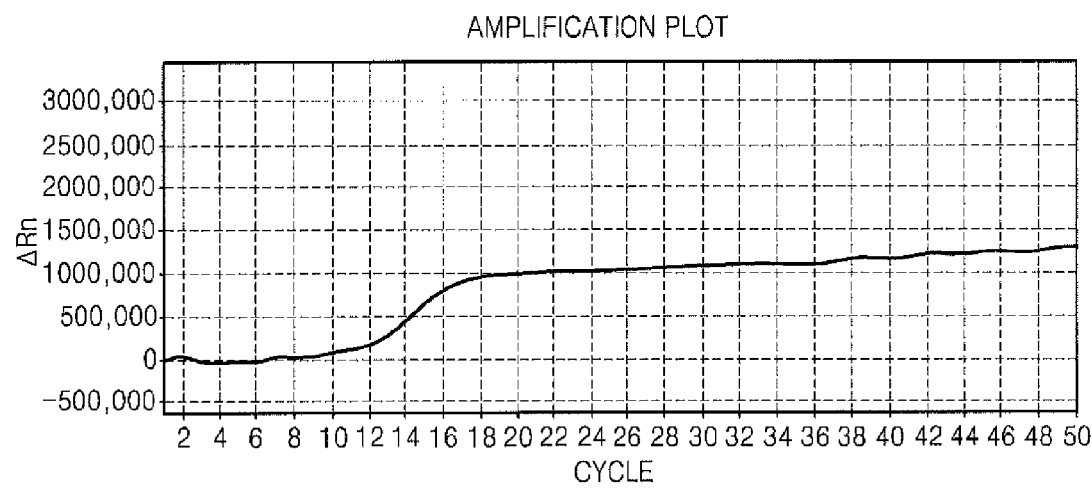
Figure 23:
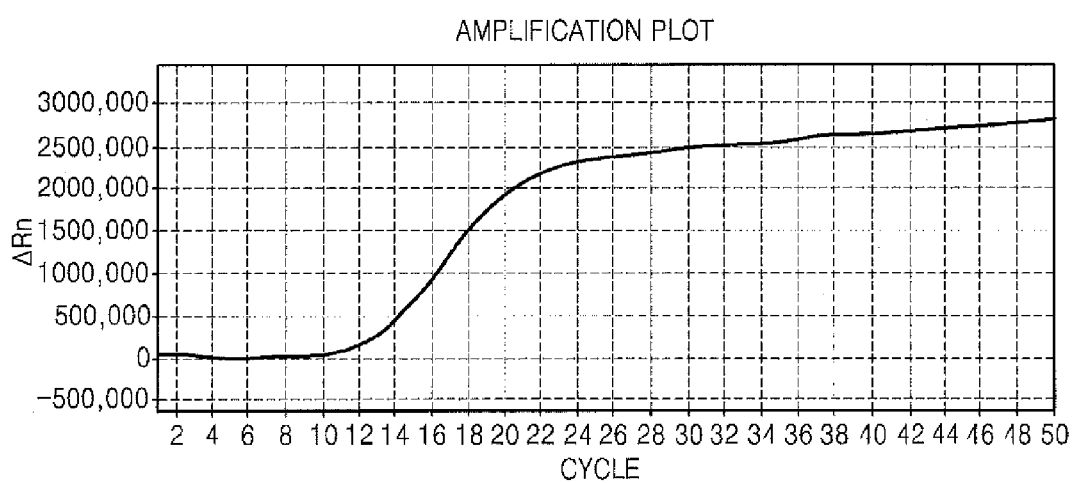
Figure 24:
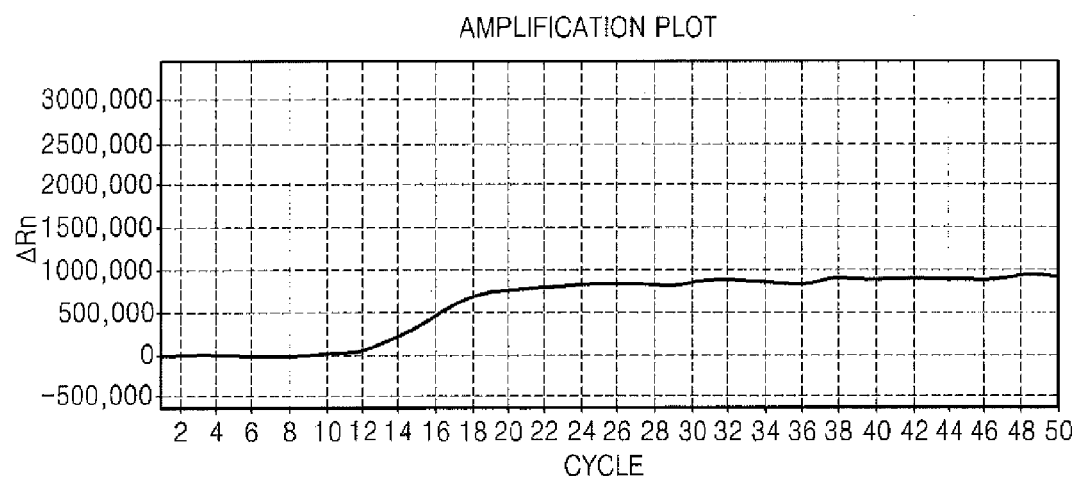
FIGS. 24 to 29 show the experimental results of amplifying the e13a3 target nucleotide sequence by using the primer set no. of 6-11.
Figure 25:
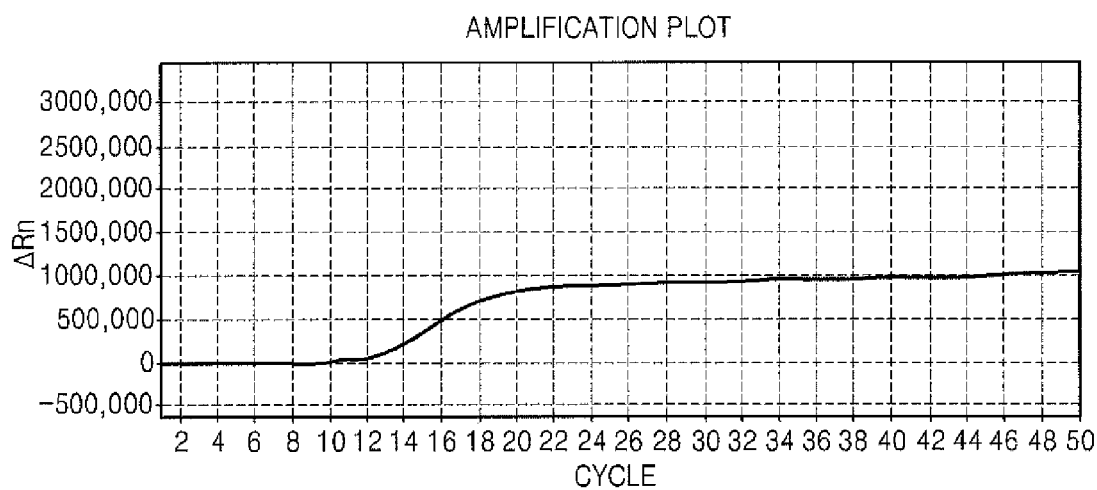
Figure 26:
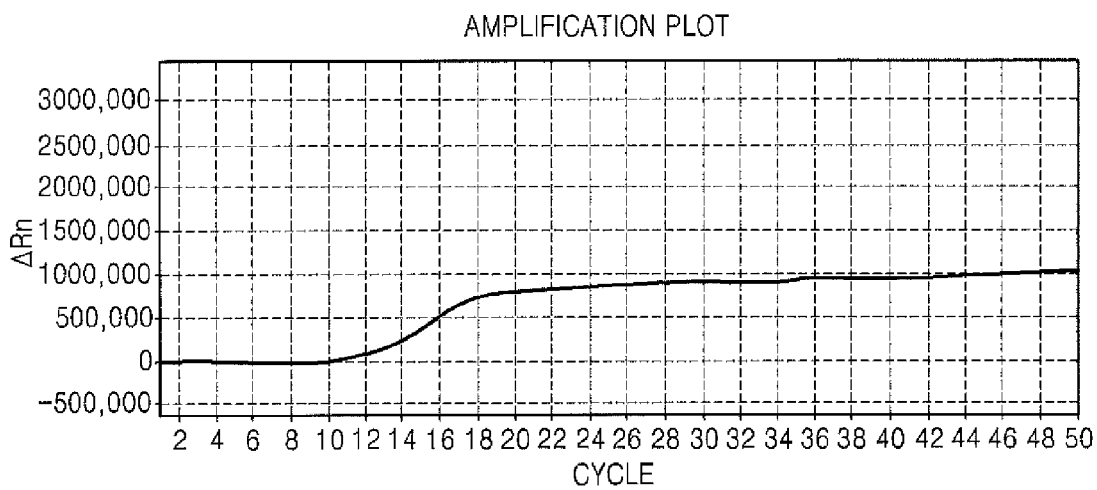
Figure 27:
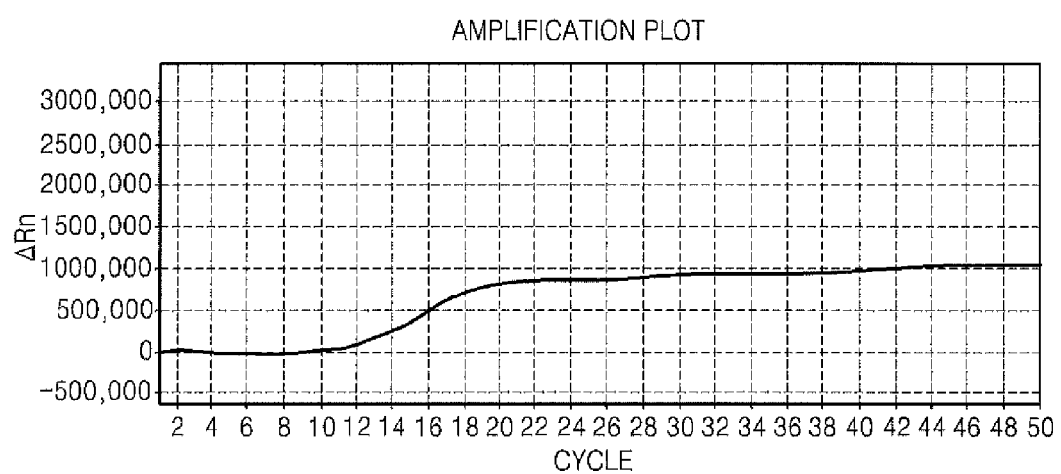
Figure 28:
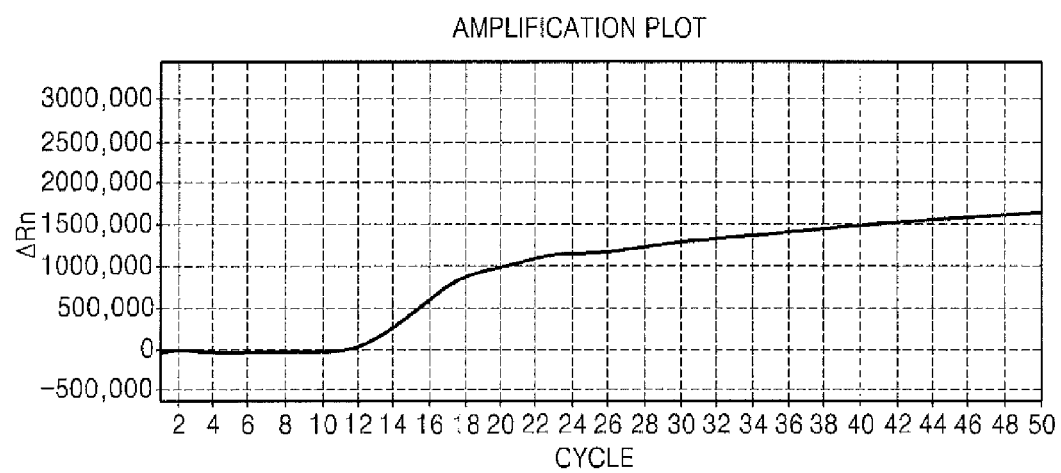
Figure 29:
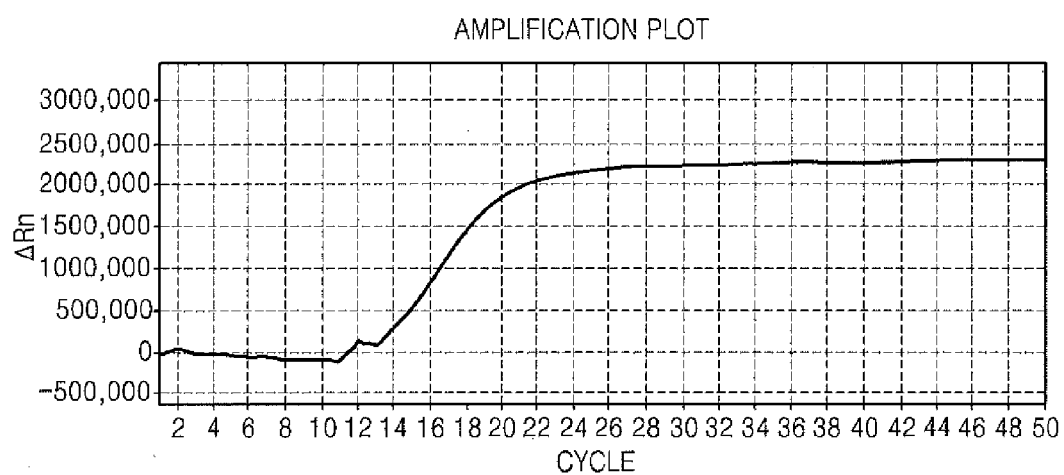
Figure 30:
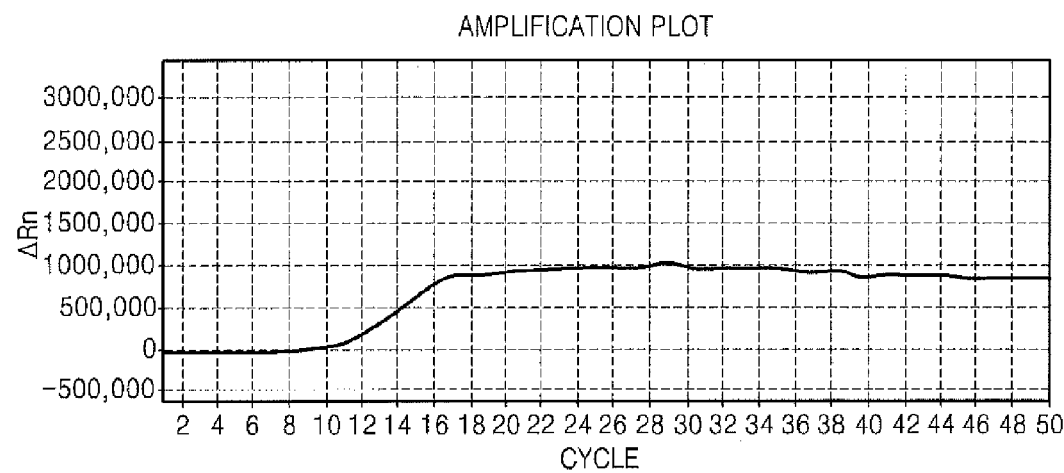
FIGS. 30 to 34 show the experimental results of amplifying the e1a2 target nucleotide sequence by using the primer set no. of 12-16.
Figure 31:
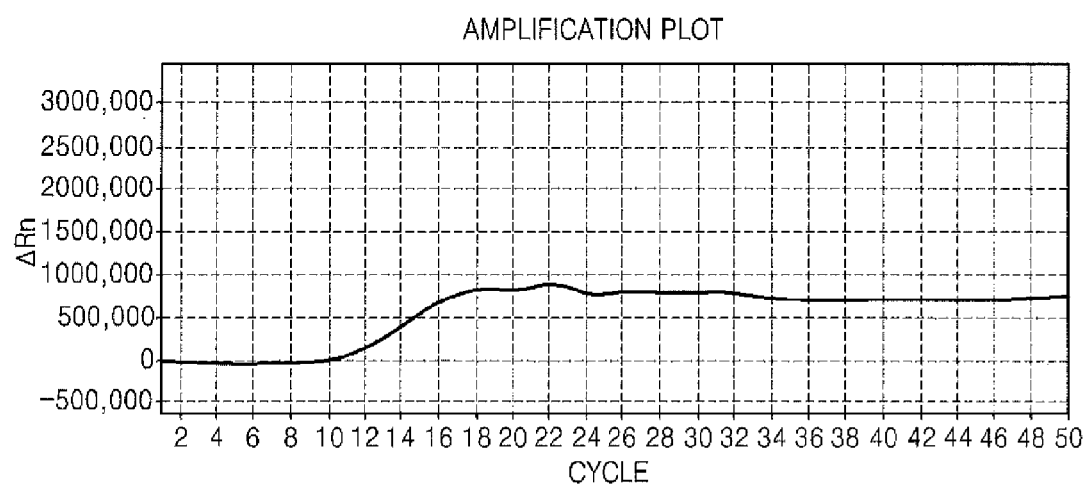
Figure 32:
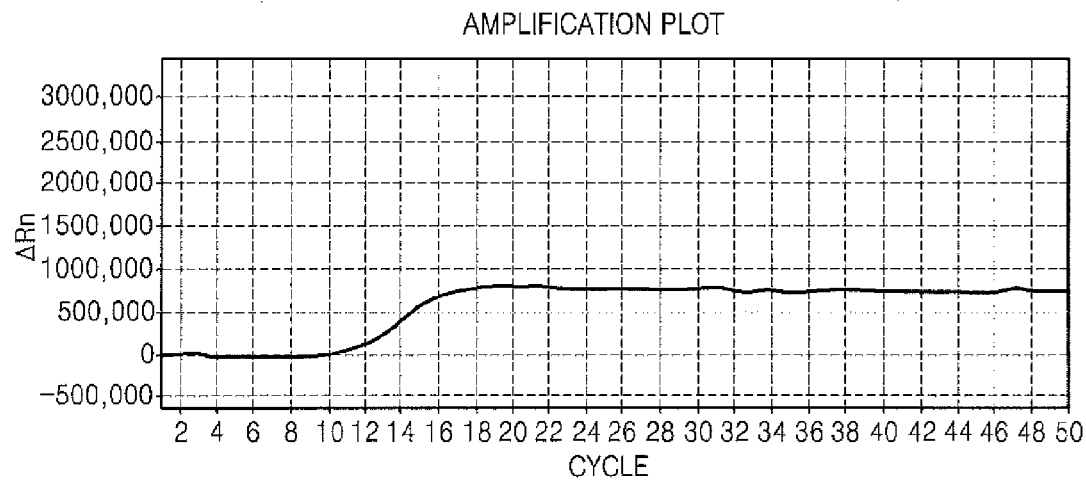
Figure 33:
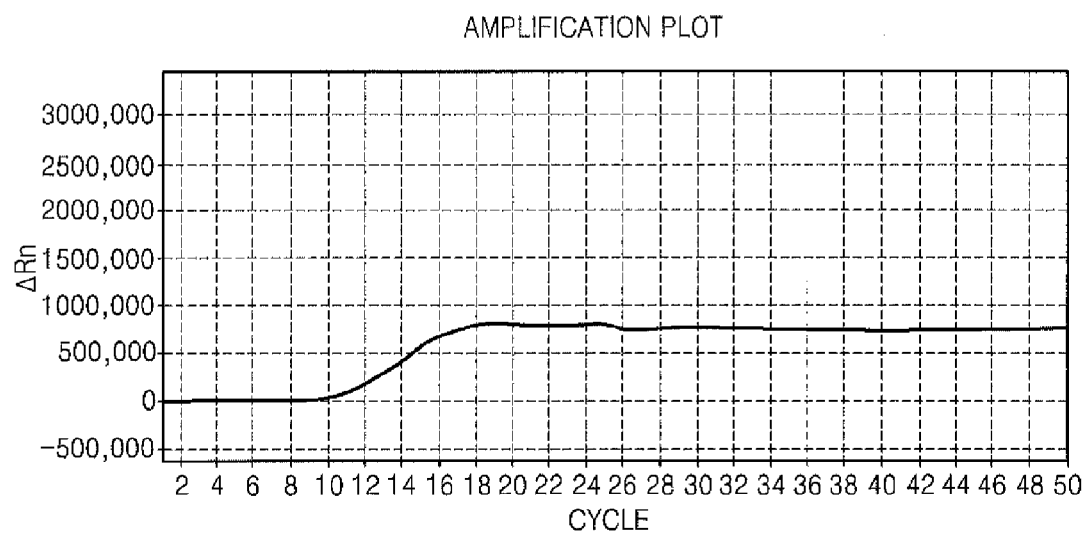
Figure 34:
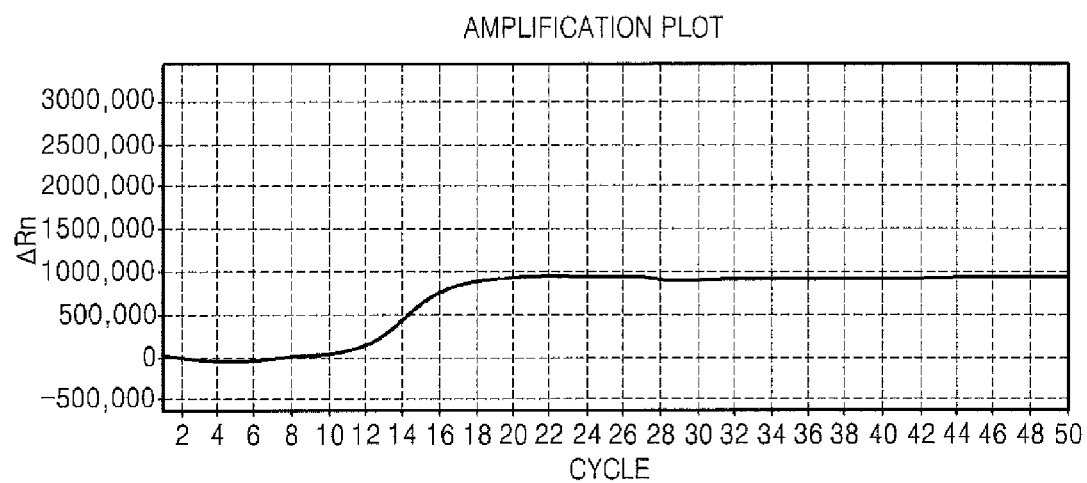

The primer and probe prepared according to Example 1, amplification buffer (32 mM HEPES-KOH, pH 7.8, 100 mM potassium acetate, 4 mM magnesium acetate, 0.11% bovine serum albumin, 1% dimethyl sulfoxide), dUTP/NTP mix (80 µM of each dGTP, dCTP, dATP and 160 µM of dUTP), 2.5 units of *Thermus aquaticus* DNA polymerase, 1 unit of *Pyrococcus furiosis* RNase HII, and 0.1 unit of uracil-N-glycosylase were used to perform a PCR in RABI7500 (Applied Biosystem) according to the following cycling protocol: initial denaturation at 95° C. for 5 minutes; 50 cycles of denaturation at 95° C. for 10 seconds, annealing at 65° C. for 10 seconds, and amplification at 72° C. for 40 seconds; final extension at 72° C. for 5 min. FAM emission was monitored when the temperature was 65° C. (Refer to FIGS. 1 to 34).

INDUSTRIAL APPLICABILITY

When the primer set and the probe according to one embodiment of the present invention are used in comparison with the concentration for a general PCR, a chronic myelogenous leukemia (CML) gene at a very low concentration may be easily detected. Therefore, the primer-probe set according to one embodiment of the present invention may be used to detect expression of a CML gene after performing a reverse transcription PCR.

What is claimed is:

1. A method of detecting an e13a2, e14a2, e13a3, or e14a3 breakpoint of a CML gene, the method comprising:
obtaining DNA from a sample;
mixing at least one primer set, a cleavable probe of SEQ ID NO: 33, and the obtained DNA sample to prepare a mixed sample,
wherein the at least one primer set is selected from the group consisting of
a tenth primer set including a primer comprising a nucleic acid of SEQ ID NO: 19 and a primer comprising a nucleic acid of SEQ ID NO: 20; and
an eleventh primer set including a primer comprising a nucleic acid of SEQ ID NO: 21 and a primer comprising a nucleic acid of SEQ ID NO: 22;
mixing a polymerase, an RNase, and an amplification buffer with the mixed sample to amplify the DNA; and
detecting an increase of a signal emitted from a label on the probe;
wherein an e13a2, e14a2, e13a3, or e14a3 breakpoint of the CML gene is detected.

2. The method of detecting a CML gene of claim 1, the method further comprising:
mixing at least one primer set selected from the group consisting of a first primer set including a primer comprising a nucleic acid of SEQ ID NO: 1 and a primer comprising a nucleic acid of SEQ ID NO: 2;
a second primer set including a primer comprising a nucleic acid of SEQ ID NO: 3 and a primer comprising a nucleic acid of SEQ ID NO: 4;
a third primer set including a primer comprising a nucleic acid of SEQ ID NO: 5 and a primer comprising a nucleic acid of SEQ ID NO: 6;
a fourth primer set including a primer comprising a nucleic acid of SEQ ID NO: 7 and a primer comprising a nucleic acid of SEQ ID NO: 8;
a fifth primer set including a primer comprising a nucleic acid of SEQ ID NO: 9 and a primer comprising a nucleic acid of SEQ ID NO: 10;
a sixth primer set including a primer comprising a nucleic acid of SEQ ID NO: 11 and a primer comprising a nucleic acid of SEQ ID NO: 12;
a seventh primer set including a primer comprising a nucleic acid of SEQ ID NO: 13 and a primer comprising a nucleic acid of SEQ ID NO: 14;
an eighth primer set including a primer comprising a nucleic acid of SEQ ID NO: 15 and a primer comprising a nucleic acid of SEQ ID NO: 16;
a ninth primer set including a primer comprising a nucleic acid of SEQ ID NO: 17 and a primer comprising a nucleic acid of SEQ ID NO: 18;

a twelfth primer set including a primer comprising a nucleic acid of SEQ ID NO: 23 and a primer comprising a nucleic acid of SEQ ID NO: 24;
a thirteenth primer set including a primer comprising a nucleic acid of SEQ ID NO: 25 and a primer comprising a nucleic acid of SEQ ID NO: 26;
a fourteenth primer set including a primer comprising a nucleic acid of SEQ ID NO: 27 and a primer comprising a nucleic acid of SEQ ID NO: 28;
a fifteenth primer set including a primer comprising a nucleic acid of SEQ ID NO: 29 and a primer comprising a nucleic acid of SEQ ID NO: 30; and
a sixteenth primer set including a primer comprising a nucleic acid of SEQ ID NO: 31 and a primer comprising a nucleic acid of SEQ ID NO: 32.

3. The method of detecting a CML gene of claim 1, wherein the CML gene is e13a2, e14a2, e13a3, or e14a3 breakpoint of a BCR-ABL fusion gene.

4. The method of claim 2, further comprising detecting an e19a2 breakpoint of the CML gene, wherein the CML gene is e19a2 breakpoint of a BCR-ABL fusion gene,
wherein the primer set is at least one primer set selected from the group consisting of
a first primer set including a primer comprising a nucleic acid of SEQ ID NO: 1 and a primer comprising a nucleic acid of SEQ ID NO: 2;
a second primer set including a primer comprising a nucleic acid of SEQ ID NO: 3 and a primer comprising a nucleic acid of SEQ ID NO: 4;
a third primer set including a primer comprising a nucleic acid of SEQ ID NO: 5 and a primer comprising a nucleic acid of SEQ ID NO: 6;
a fourth primer set including a primer comprising a nucleic acid of SEQ ID NO: 7 and a primer comprising a nucleic acid of SEQ ID NO: 8; and
a fifth primer set including a primer comprising a nucleic acid of SEQ ID NO: 9 and a primer comprising a nucleic acid of SEQ ID NO: 10.

5. The method of detecting a CML gene of claim 2, wherein the CML gene is e13a2, e14a2, e13a3, or e14a3breakpoint of a BCR-ABL fusion gene,
wherein the primer set is at least one primer set selected from the group consisting of
a sixth primer set including a primer comprising a nucleic acid of SEQ ID NO: 11 and a primer comprising a nucleic acid of SEQ ID NO: 12;
a seventh primer set including a primer comprising a nucleic acid of SEQ ID NO: 13 and a primer comprising a nucleic acid of SEQ ID NO: 14;
an eighth primer set including a primer comprising a nucleic acid of SEQ ID NO: 15 and a primer comprising a nucleic acid of SEQ ID NO: 16; and
a ninth primer set including a primer comprising a nucleic acid of SEQ ID NO: 17 and a primer comprising a nucleic acid of SEQ ID NO: 18.

6. The method of claim 2, further comprising detecting an e1a2 breakpoint of the CML gene, wherein the CML gene is e1a2 breakpoint of a BCR-ABL fusion gene,
wherein the primer set is at least one primer set selected from the group consisting of
a twelfth primer set including a primer comprising a nucleic acid of SEQ ID NO: 23 and a primer comprising a nucleic acid of SEQ ID NO: 24;
a thirteenth primer set including a primer comprising a nucleic acid of SEQ ID NO: 25 and a primer comprising a nucleic acid of SEQ ID NO: 26;
fourteenth primer set including a primer comprising a nucleic acid of SEQ ID NO: 27 and a primer comprising a nucleic acid of SEQ ID NO: 28;
a fifteenth primer set including a primer comprising a nucleic acid of SEQ ID NO: 29 and a primer comprising a nucleic acid of SEQ ID NO: 30; and
a sixteenth primer set including a primer comprising a nucleic acid of SEQ ID NO: 31 and a primer comprising a nucleic acid of SEQ ID NO: 32.

7. The method of detecting a CML gene of claim 1, wherein the method is a multiplex method of detecting a CML gene.

8. The method of detecting a CML gene of claim 2, wherein the method is a multiplex method of detecting a CML gene.

9. The method of detecting a CML gene of claim 1, wherein the cleavable probe is labeled with a detectable material at both ends of the probe.

10. The method of detecting a CML gene of claim 2, wherein the cleavable probe is labeled with a detectable material at both ends of the probe.

11. The method of detecting a CML gene of claim 1, wherein the polymerase is a thermostable polymerase.

12. The method of detecting a CML gene of claim 11, wherein the polymerase is a thermostable DNA polymerase.

* * * * *

SEQUENCE LISTING

<160> NUMBER OF SEQ ID NOS: 39

<210> SEQ ID NO 1
<211> LENGTH: 20
<212> TYPE: DNA
<213> ORGANISM: Artificial Sequence

```
<220> FEATURE:
<223> OTHER INFORMATION: a specific forward primer for amplifying break
      point BCR-e19 of CML

<400> SEQUENCE: 1
gaggtgggca tctaccgcgt                                                  20

<210> SEQ ID NO 2
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 2
gctgccattg atcccgctgc                                                  20

<210> SEQ ID NO 3
<211> LENGTH: 20
<212> TYPE: DNA
<213> ORGANISM: Artificial Sequence
<220> FEATURE:
<223> OTHER INFORMATION: a specific forward primer for amplifying break
      point BCR-e19 of CML

<400> SEQUENCE: 3
tctaccgcgt gtccggtgtg                                                  20

<210> SEQ ID NO 4
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 4
gctgccattg atcccgctgc                                                  20

<210> SEQ ID NO 5
<211> LENGTH: 20
<212> TYPE: DNA
<213> ORGANISM: Artificial Sequence
<220> FEATURE:
<223> OTHER INFORMATION: a specific forward primer for amplifying break
      point BCR-e19 of CML

<400> SEQUENCE: 5
tgcgtggagg agatcgagcg                                                  20

<210> SEQ ID NO 6
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 6
gctgccattg atcccgctgc                                                  20

<210> SEQ ID NO 7
<211> LENGTH: 20
<212> TYPE: DNA
<213> ORGANISM: Artificial Sequence
<220> FEATURE:
```

<223> OTHER INFORMATION: a specific forward primer for amplifying break
      point BCR-e19 of CML

<400> SEQUENCE: 7
aggtgggcat ctaccgcgtg                                                    20

<210> SEQ ID NO 8
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 8
gctgccattg atcccgctgc                                                    20

<210> SEQ ID NO 9
<211> LENGTH: 20
<212> TYPE: DNA
<213> ORGANISM: Artificial Sequence
<220> FEATURE:
<223> OTHER INFORMATION: a specific forward primer for amplifying break
      point BCR-e19 of CML

<400> SEQUENCE: 9
tgcgtggagg agatcgagcg                                                    20

<210> SEQ ID NO 10
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 10
attgcgggac acaggcccat                                                    20

<210> SEQ ID NO 11
<211> LENGTH: 24
<212> TYPE: DNA
<213> ORGANISM: Artificial Sequence
<220> FEATURE:
<223> OTHER INFORMATION: a specific forward primer for amplifying break
      point BCR-e13 of CML

<400> SEQUENCE: 11
agcttctccc tgacatccgt ggag                                               24

<210> SEQ ID NO 12
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 12
attgcgggac acaggcccat                                                    20

<210> SEQ ID NO 13
<211> LENGTH: 24
<212> TYPE: DNA
<213> ORGANISM: Artificial Sequence
<220> FEATURE:
<223> OTHER INFORMATION: a specific forward primer for amplifying break point BCR-e13 of CML

<400> SEQUENCE: 13
ctgcagatgc tgaccaactc gtgt                                          24

<210> SEQ ID NO 14
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 14
attgcgggac acaggcccat                                               20

<210> SEQ ID NO 15
<211> LENGTH: 26
<212> TYPE: DNA
<213> ORGANISM: Artificial Sequence
<220> FEATURE:
<223> OTHER INFORMATION: a specific forward primer for amplifying break
      point BCR-e13 of CML

<400> SEQUENCE: 15
gatgctgacc aactcgtgtg tgaaac                                        26

<210> SEQ ID NO 16
<211> LENGTH: 21
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 16
cattgcggga cacaggccca t                                             21

<210> SEQ ID NO 17
<211> LENGTH: 24
<212> TYPE: DNA
<213> ORGANISM: Artificial Sequence
<220> FEATURE:
<223> OTHER INFORMATION: a specific forward primer for amplifying break
      point BCR-e13 of CML

<400> SEQUENCE: 17
agcttctccc tgacatccgt ggag                                          24

<210> SEQ ID NO 18
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 18
gctgccattg atcccgctgc                                               20

<210> SEQ ID NO 19
<211> LENGTH: 24
<212> TYPE: DNA
<213> ORGANISM: Artificial Sequence
<220> FEATURE:
<223> OTHER INFORMATION: a specific forward primer for amplifying break
      point BCR-e13 of CML

```
<400> SEQUENCE: 19
ctgcagatgc tgaccaactc gtgt                                          24

<210> SEQ ID NO 20
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 20
gctgccattg atcccgctgc                                               20

<210> SEQ ID NO 21
<211> LENGTH: 26
<212> TYPE: DNA
<213> ORGANISM: Artificial Sequence
<220> FEATURE:
<223> OTHER INFORMATION: a specific forward primer for amplifying break
      point BCR-e13 of CML

<400> SEQUENCE: 21
gatgctgacc aactcgtgtg tgaaac                                        26

<210> SEQ ID NO 22
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 22
gctgccattg atcccgctgc                                               20

<210> SEQ ID NO 23
<211> LENGTH: 20
<212> TYPE: DNA
<213> ORGANISM: Artificial Sequence
<220> FEATURE:
<223> OTHER INFORMATION: a specific forward primer for amplifying break
      point BCR-e1 of CML

<400> SEQUENCE: 23
cataagcggc accggcactg                                               20

<210> SEQ ID NO 24
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 24
attgcgggac acaggcccat                                               20

<210> SEQ ID NO 25
<211> LENGTH: 20
<212> TYPE: DNA
<213> ORGANISM: Artificial Sequence
<220> FEATURE:
<223> OTHER INFORMATION: a specific forward primer for amplifying break
      point BCR-e1 of CML
```

<400> SEQUENCE: 25
actgcccggt tgtcgtgtcc                                                    20

<210> SEQ ID NO 26
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 26
attgcgggac acaggcccat                                                    20

<210> SEQ ID NO 27
<211> LENGTH: 20
<212> TYPE: DNA
<213> ORGANISM: Artificial Sequence
<220> FEATURE:
<223> OTHER INFORMATION: a specific forward primer for amplifying break
      point BCR-e1 of CML

<400> SEQUENCE: 27
cactgcccgg ttgtcgtgtc                                                    20

<210> SEQ ID NO 28
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 28
gctgccattg atcccgctgc                                                    20

<210> SEQ ID NO 29
<211> LENGTH: 20
<212> TYPE: DNA
<213> ORGANISM: Artificial Sequence
<220> FEATURE:
<223> OTHER INFORMATION: a specific forward primer for amplifying break
      point BCR-e1 of CML

<400> SEQUENCE: 29
ccataagcgg caccggcact                                                    20

<210> SEQ ID NO 30
<211> LENGTH: 20
<212> TYPE: DNA
<213> ORGANISM: Artificial Sequence
<220> FEATURE:
<223> OTHER INFORMATION: a specific reverse primer for amplifying point
      ABL-a3 of CML

<400> SEQUENCE: 30
attgcgggac acaggcccat                                                    20

<210> SEQ ID NO 31
<211> LENGTH: 20
<212> TYPE: DNA
<213> ORGANISM: Artificial Sequence
<220> FEATURE:
<223> OTHER INFORMATION: a specific forward primer for amplifying break
      point BCR-e1 of CML

<400> SEQUENCE: 31

```
cccggttgtc gtgtccgagg                                                20
```

<210> SEQ ID NO 32
<211> LENGTH: 20
<212> TYPE: DNA
<213> ORGANISM: Artificial Sequence
<220> FEATURE:
<223> OTHER INFORMATION: a specific reverse primer for amplifying point
    ABL-a3 of CML

<400> SEQUENCE: 32

```
gctgccattg atcccgctgc                                                20
```

<210> SEQ ID NO 33
<211> LENGTH: 24
<212> TYPE: DNA
<213> ORGANISM: Artificial Sequence
<220> FEATURE:
<223> OTHER INFORMATION: a specific probe for detecting break point of
    CML
<220> FEATURE:
<223> OTHER INFORMATION: 'guga' is RNA

<400> SEQUENCE: 33

```
ggggaatggt gugaagccca aacc                                           24
```

<210> SEQ ID NO 34
<211> LENGTH: 639
<212> TYPE: DNA
<213> ORGANISM: Artificial Sequence
<220> FEATURE:
<223> OTHER INFORMATION: sequences including e14a2 region

<400> SEQUENCE: 34

```
agcttctccc tgacatccgt ggagctgcag atgctgacca actcgtgtgt gaaactccag    60
actgtccaca gcattccgct gaccatcaat aaggaagatg atgagtctcc ggggctctat   120
gggtttctga atgtcatcgt ccactcagcc actggattta agcagagttc aaaagccctt   180
cagcggccag tagcatctga ctttgagcct caggttctga gtgaagccgc tcgttggaac   240
tccaaggaaa accttctcgc tggacccagt gaaaatgacc ccaaccttt cgttgcactg   300 tatgatttg tggccagtgg agataacact ctaagcataa ctaaaggtga aaagctccgg   360
gtcttaggct ataatcacaa tggggaatgg tgtgaagccc aaaccaaaaa tggccaaggc   420
tgggtcccaa gcaactacat cacgccagtc aacagtctgg agaaacactc ctggtaccat   480
gggcctgtgt cccgcaatgc cgctgagtat ctgctgagca gcgggatcaa tggcagcttc   540
ttggtgcgtg agagtgagag cagtcctggc cagaggtcca tctcgctgag atacgaaggg   600
agggtgtacc attacaggat caacactgct tctgatggc                          639
```

<210> SEQ ID NO 35
<211> LENGTH: 564
<212> TYPE: DNA
<213> ORGANISM: Artificial Sequence
<220> FEATURE:
<223> OTHER INFORMATION: sequences including e13a2 region

<400> SEQUENCE: 35

```
agcttctccc tgacatccgt ggagctgcag atgctgacca actcgtgtgt gaaactccag    60
actgtccaca gcattccgct gaccatcaat aaggaagaag cccttcagcg gccagtagca   120
tctgactttg agcctcaggg tctgagtgaa gccgctcgtt ggaaatccaa ggaaaacctt   180
```

```
ctcgctggac ccagtgaaaa tgaccccaac cttttcgttg cactgtatga ttttgtggcc      240
agtggagata acactctaag cataactaaa ggtgaaaagc tccgggtctt aggctataat      300
cacaatgggg aatggtgtga agcccaaacc aaaaatggcc aaggctgggt cccaagcaac      360
tacatcacgc cagtcaacag tctggagaaa cactcctggt accatgggcc tgtgtcccgc      420
aatgccgctg agtatctgct gagcagcggg atcaatggca gcttcttggt gcgtgagagt      480
gagagcagtc ctggccagag gtccatctcg ctgagatacg aagggagggt gtaccattac      540
aggatcaaca ctgcttctga tggc                                             564

<210> SEQ ID NO 36
<211> LENGTH: 465
<212> TYPE: DNA
<213> ORGANISM: Artificial Sequence
<220> FEATURE:
<223> OTHER INFORMATION: sequences including e14a3 region

<400> SEQUENCE: 36
agcttctccc tgacatccgt ggagctgcag atgctgacca actcgtgtgt gaaactccag       60
actgtccaca gcattccgct gaccatcaat aaggaagatg atgagtctcc ggggctctat      120
gggtttctga atgtcatcgt ccactcagcc actggattta agcagagttc aagtgaaaag      180
ctccgggtct taggctataa tcacaatggg aatggtgtg aagcccaaac caaaaatggc      240
caaggctggg tcccaagcaa ctacatcacg ccagtcaaca gtctggagaa acactcctgg      300
taccatgggc ctgtgtcccg caatgccgct gagtatctgc tgagcagcgg gatcaatggc      360
agcttcttgg tgcgtgagag tgagagcagt cctggccaga ggtccatctc gctgagatac      420
gaagggaggg tgtaccatta caggatcaac actgcttctg atggc                     465

<210> SEQ ID NO 37
<211> LENGTH: 390
<212> TYPE: DNA
<213> ORGANISM: Artificial Sequence
<220> FEATURE:
<223> OTHER INFORMATION: sequences including e13a3 region

<400> SEQUENCE: 37
agcttctccc tgacatccgt ggagctgcag atgctgacca actcgtgtgt gaaactccag       60
actgtccaca gcattccgct gaccatcaat aaggaaggtg aaaagctccg ggtcttaggc      120
tataatcaca atggggaatg gtgtgaagcc caaaccaaaa atggccaagg ctgggtccca      180
agcaactaca tcacgccagt caacagtctg gagaaacact cctggtacca tgggcctgtg      240
tcccgcaatg ccgctgagta tctgctgagc agcgggatca atggcagctt cttggtgcgt      300
gagagtgaga gcagtcctgg ccagaggtcc atctcgctga gatacgaagg gagggtgtac      360
cattacagga tcaacactgc ttctgatggc                                       390

<210> SEQ ID NO 38
<211> LENGTH: 625
<212> TYPE: DNA
<213> ORGANISM: Artificial Sequence
<220> FEATURE:
<223> OTHER INFORMATION: sequences including e1a2 region

<400> SEQUENCE: 38
gcaacagtcc ttcgacagca gcagtccccc cacgccgcag tgccataagc ggcaccggca       60
ctgcccggtt gtcgtgtccg aggccaccat cgtgggcgtc cgcaagaccg gcagatctg      120 gcccaacgat ggcgagggcg ccttccatgg agacgcagaa gcccttcagc ggccagtagc      180
```

```
atctgactttt gagcctcagg gtctgagtga agccgctcgt tggaactcca aggaaaacct    240
tctcgctgga cccagtgaaa atgacccccaa ccttttcgtt gcactgtatg attttgtggc    300
cagtggagat aacactctaa gcataactaa aggtgaaaag ctccgggtct taggctataa    360
tcacaatggg gaatggtgtg aagcccaaac caaaaatggc caaggctggg tcccaagcaa    420
ctacatcacg ccagtcaaca gtctggagaa acactcctgg taccatgggc ctgtgtcccg    480
caatgccgct gagtatctgc tgagcagcgg gatcaatggc agcttcttgg tgcgtgagag    540
tgagagcagt cctggccaga ggtccatctc gctgagatac gaagggaggg tgtaccatta    600
caggatcaac actgcttctg atggc                                          625
```

```
<210> SEQ ID NO 39
<211> LENGTH: 600
<212> TYPE: DNA
<213> ORGANISM: Artificial Sequence
<220> FEATURE:
<223> OTHER INFORMATION: sequences including e19a2 region

<400> SEQUENCE: 39
aggtccaagg tgccctacat cgtgcgccag tgcgtggagg agatcgagcg ccgaggcatg     60
gaggaggtgg gcatctaccg cgtgtccggt gtggccacgg acatccaggc actgaaggca    120
gccttcgacg tcaaagccct tcagcggcca gtagcatctg actttgagcc tcagggtctg    180
agtgaagccg ctcgttggaa ctccaaggaa aaccttctcg ctggacccag tgaaaatgac    240
cccaaccttt tcgttgcact gtatgatttt gtggccagtg gagataacac tctaagcata    300
actaaaggtg aaaagctccg ggtcttaggc tataatcaca atggggaatg gtgtgaagcc    360
caaaccaaaa atggccaagg ctgggtccca agcaactaca tcacgccagt caacagtctg    420
gagaaacact cctggtacca tgggcctgtg tcccgcaatg ccgctgagta tctgctgagc    480
agcgggatca atggcagctt cttggtgcgt gagagtgaga gcagtcctgg ccagaggtcc    540
atctcgctga gatacgaagg gagggtgtac cattacagga tcaacactgc ttctgatggc    600
```